US006903247B2

(12) United States Patent
Aldwinckle et al.

(10) Patent No.: US 6,903,247 B2
(45) Date of Patent: Jun. 7, 2005

(54) CONSTITUTIVE α-TUBULIN PROMOTER FROM COFFEE PLANTS AND USES THEREOF

(75) Inventors: Herbert S. Aldwinckle, Geneva, NY (US); Alvaro L. Gaitan, Manizales (CO)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/197,280

(22) Filed: Jul. 16, 2002

(65) Prior Publication Data

US 2003/0163837 A1 Aug. 28, 2003

Related U.S. Application Data

(63) Continuation-in-part of application No. 09/545,686, filed on Apr. 7, 2000, now Pat. No. 6,441,273.
(60) Provisional application No. 60/180,934, filed on Feb. 8, 2000.

(51) Int. Cl.$^7$ .............................. A01H 5/00; A01H 5/10; C12N 15/82; C12N 15/11
(52) U.S. Cl. .................... 800/298; 800/278; 435/252.3; 435/419; 435/320.1; 536/24.1
(58) Field of Search .............................. 435/252.3, 419, 435/320.1; 800/278, 298, 320, 320.1, 320.2, 320.3, 322, 31.7, 317.1, 317.2, 317.3, 317.4, 306, 310, 309, 307, 312, 315, 294, 293; 536/24.1; 424/93.2; 526/24.1

(56) References Cited

U.S. PATENT DOCUMENTS

| | | | |
|---|---|---|---|
| 5,334,529 A | | 8/1994 | Adams et al. |
| 5,608,143 A | | 3/1997 | Hershey et al. |
| 5,750,386 A | | 5/1998 | Conkling et al. |
| 5,792,921 A | | 8/1998 | Londesborough et al. |
| 5,874,269 A | | 2/1999 | Stiles et al. |
| 5,939,288 A | | 8/1999 | Thornburg |
| 6,008,436 A | | 12/1999 | Conkling et al. |
| 6,441,273 B1 | * | 8/2002 | Aldwinckle et al. ........ 800/278 |

FOREIGN PATENT DOCUMENTS

| | | |
|---|---|---|
| EP | 0 388 186 A1 | 9/1990 |
| WO | WO 99/02688 | 1/1999 |

OTHER PUBLICATIONS

Jefferson et al, 1987, GenBank Accession No. U12639.*
Brierley et al, 1995, Plant Mol. Biol. 27:715–727.*
Boxtel et al., "Transient Expression of β–Glucuronidase Following Biolistic Delivery of Foreign DNA into Coffee Tissues," *Plant Cell Reports* 14:748–752 (1995).
Marraccini et al., "Molecular Cloning of the Complete 11S Seed Storage Protein Gene of *Coffea arabica* and Promoter Analysis in Transgenic Tobacco Plants," *Plant Physiol. Biochem.* 37(4):273–282 (1999).
Rogers et al., "An 11S–Type Storage Protein from *Coffea arabica* L. Endosperm: Biochemical Characterization, Promoter Function and Expression During Grain Maturation," *Association Scientifique Internationale du Café* pp. 161–168 (1997).
Elkind et al., "Abnormal Plant Development and Down–Regulation of Phenylpropanoid Biosynthesis in Transgenic Tobacco Containing Heterologous Phenylalanine Ammonia–Lyase Gene," *Proceedings of the National Academy of Sciences of the USA* 87:9057–9061 (1990).
Hahlbrock et al., "Physiology and Molecular Biology of the Phenylpropanoid Metabolism," *Annual Review of Plant Physiology and Plant Molecular Biology* 40:347–369 (1989).
Hammond–Kosack et al., "Resistance Gene–Dependent Plant Defense Responses," *The Plant Cell* 8:1773–1791 (1996).
Joos et al., "Phenylalanine Ammonia Lyase in Potato (*Solanum tuberosum* L.), Genomic Complexity, Structural Comparison of Two Selected Clones and Modes Of Expression," *European Journal of Biochemistry* 204:621–629 (1992).
Lashermes et al., "Inheritance and Restriction Fragment Length Polymorphism of Chloroplast DNA in the Genus *Coffea* L.," *Theoretical and Applied Genetics* 93:626–632 (1996).
Lois et al., "A Phenylalanine Ammonia–Lyase Gene from Parsley: Structure, Regulation and Identification of Elicitor and Light Responsive Cis–Acting Elements," *EMBO Journal* 8:1641–1648 (1989).
Ohl et al., "Functional Properties of a Phenylalanine Ammonia–Lyase Promoter from *Arabidopsis,*" *The Plant Cell* 2:837–848 (1990).
Rojas et al., "Stimulation of Lipoxygenase Activity by Cotyledonary Leaves of Coffee Reacting Hypersensitively to the Coffee Leaf Rust," *Physiological and Molecular Plant Pathology* 43:209–219 (1993).

(Continued)

*Primary Examiner*—Anne Kubelik
(74) *Attorney, Agent, or Firm*—Nixon Peabody LLP

(57) ABSTRACT

The present invention relates to the isolation and characterization of a constitutive α-tubulin promoter from a coffee plant. The isolated promoter of the present invention is capable of inducing the expression of a protein encoded by a DNA molecule that is operably linked to the promoter in a DNA construct. The present invention also relates to DNA constructs expression systems, host cells, and transgenic plants and plant seeds containing the promoter of the invention. The present invention also relates to a method of making a transgenic plant and a method of directing protein expression in plants that involve transforming a plant cell with a DNA construct containing the promoter of the invention.

19 Claims, 15 Drawing Sheets

OTHER PUBLICATIONS

Whetten et al., "Phenylalanine Ammonia Lyase from Lobiolly Pine: Purification of the Enzyme and Isolation of Complementary DNA Clones," *Plant Physiology* 98:380–386 (1992).

Zhu et al., "Cloning and Functional Expression of a cDNA Encoding Coffee Bean Alpha–Galactosidase," *Gene* 140:227–231 (1994).

Dong et al., "Induction of *Arabidopsis* Defense Genes by Virulent and Avirulent *Pseudomonas syringae* Strains and by a Cloned Avirulence Gene," *The Plant Cell* 3:61–72 (1991).

Sharma et al., "Ozone Induced Expression of Stress Related Genes in *Arabidopsis thaliana.*" *Plant Physiology* 105:1089–1096 (1994).

Hartley et al., "Biochemical Aspects and Significance of the Rapidly Induced Accumulation of Phenolics in Birch Foliage," in Tallamy, eds., *Phytochemical Induction in Herbivores*, New York: John Wiley & Sons, Inc., pp. 105–132 (1991).

Gaitan et al., "Cloning and Evaluation of Gene Promoters in *Coffea arabica,*" *Phytopathology* 87: pp. S31.

* cited by examiner

| Exon 1 | Intron 1 | Exon 2 | Intron 2 | Exon 3 |
|---|---|---|---|---|
| 72-111 bp | 83-1725 bp | 213-234 bp | 78-96 bp | 198-369 bp |

FIG. 1A

```
GNNNNNNNNN NNCCNTNGTN NTNGCCTCTC CCCGAGCACA NNNNCTNNCC   50
GGCNNCCNNG CCCNANNCCN NNGTNTCGGC GGCNGCNCAG CCNCAGCCGC  100
CCGNCCAAGA TGAGGGAGTG CATCTCGATC CACATCGGCC AGGCCGGGAT  150
ALP-F40                    ALP-F59
CCAGGTCGGC AACGCGTGCT GGGAGCTCTA CTGCCTCGAG CATGGCATCC  200
AGCCTGATGG CCAGATGCCC AGTGACAAGA CCGTTGGGGG AGCAGATGAT  250
GCGTTCAACA CCTTCTTCAG TGAGACTGGT GCTGGCAAGC ACGTGCCCAG  300
GGCCGTCTTT GTCGATCTTG AGCCCACTGT CATTGATGAG GTGCGGACTG  350
                    ALP-R247
GTGCCTACCG CCAGCTCTTC CACCCTGAGC AGCTCATCAG TGGCAAGGAG  400
                    ALP-R304
GATGCAGCCA ACAACTTTGC CCGTGGCCAC TACACCATTG CAAGGAGAT   450
TGTTGATCTG TGCCTGGACC GTATCCGCAA GCTTGCAGAC AACTGCACTG  500
GGCTGCAGGG ATTCCTTGTG TTCAATGCTG TTGGTGGTGG AACTGGCTCT  550
GGACTTGGTT CTCTTCTGTT GGAGCGTCTC TCTGTTGATT ATGGAAAGAA  600
GTCCAAGCTT GGGNTTCACC GTGTACCCTT CCCCACAG              638
```

FIG. 1B

```
    ALP-F59
CCTGCTGGGA GCTCTACTGC CTCGAGCACG GCATCCAGGT AAATTGTCTT   50
CTATCTAACC TCTTATATTT CAGATCTGCT GTTTCTCTCA TTTTTGTTCA  100
AGGAAATGAT TCATCTTTGG TTTGATTTTG GGTGTTGTGG AATAGCCTGA  150
TGGACAAATG CCGAGCGACC ACACCGTCGG AGGCGGAGAC GACGCTTTCA  200
ACACCTTCTT CAGCGAAACC GGAGCCGGCA AACACGTTCC TCGTGCCGTG  250
TTCGTCGATC TGGAGCCCAC TGTCATCGAT GAAGTCCGAA CCGGCACCTA  300
CCGCCAACTC TTCCACCCTG AGCAGCTCAT                        350
                    ALP-R304
```

FIG. 1C

```
  ALP-F40
GTATCCAGGT CGGAAACGCC TGCTGGGAGC TCTACTGCCT CGAGCACGGC   50
ATCCAGGTAA ATTGCCTTCT ATCTAACCTC TATATTTCAG ATCTGCTGTT  100
TCTCTCATTT TTGTTCAAGG AAATGATTCA TCTTTGGTTT GATTTTGGGT  150
GTTGTGGAAT AGCCTGATGG ACAAATGCCG AGCGACCACA CCGTCGGCGG  200
CGGAGACGAC GCTTTCAACA CCTTCTTCAG CGAAACCGGA GCCGGCAAAC  250
ACGTTCCTCG TGCCGTGTTC GTTGATCTTG AACCCACTGT             290
                               ALP-R247
```

FIG. 1D

| Exon 1 | Intron 1 | Exon 2 |
|---|---|---|
| 390-477 bp | 91-1520 bp | 1746-1884 bp |

FIG. 2A

```
            PAL-F25
    ─────────────────────────▶
                              PAL-F39
                         ──────────────▶
GATCCNTTGA ACTGGGNNNT GGCNGCNGAG NCATTGAANG GNAGNCANTT   50
────▶
GGATGAAGTG AAGNGNATGG TGGCNGAGTT NAGGAAGCCG GTNGTGAAGC  100
TTGGAGGNGA GACNTTGACG ATNTCTCAGG TGGCNGCNTA TTGCNGCCAN  150
NNATGATGNT NNNNNNGTCA NGGTGGAGCT NTCNGAGGCG GCNAGNGCTG  200
GCGTTAAGGC NAGCAGTGAT TGGGTGATGG ATAGTATGAA CAAAGGGACT  250
                                     PAL-R127
                              ◀──────────────────────
                         PAL-R133
              ◀────────────────────────
GATAGCTATG GTGTCACTAC TGGCTTTCGT GCTACTTCTC ACAGGAGAAC  300
CAAGCAAGGT GGTGCTCTTC AGAAGGAGCT CATTAGGTTC TTGAATGCTG  350
GAATATTTGG CAATGGAACA GAGTCAAGTC ACACATTGCC ACACTCAGCT  400
ACAAGGGCAG CTATGCTTGT GAGAATCAAC ACTCTCCTCC AAGGATACTC  450
TGGCATCAGA TTTGAAATCT TGGAAGCCAT TACCAAATTC CTTAACCACA  500
```

FIG. 2B

```
    PAL-F39
─────────────▶
AAAGGGAGTC ATTTGGATGA AGTGAAAAAA ATGGTGAGTG AATTTAGAAA   50
ACCAGTGGTA AAACTTGGTG GTGAAACTTT AACAGTGGCA CAAGTGGCTG  100
CTATTGCTGT TAGGGACAAA AGTGCAAATG GTGTTAAAGT TGAACTTTCT  150
GAAGAGGCAA GAGCTGGTGT TAAAGCTAGT AGTGATTGGG TGATGGATAG  200
TAT                              ◀────────────────── 203
                                     PAL-R127
───
```

FIG. 2C

```
    PAL-F39
─────────────▶
AAAGGGAGTC ATTTGGATGA AGTGAAAAAA ATGGTGAGTG AATTTAGAAA   50
ACCAGTGGTA AAACTTGGTG GTGAGACTTT AACAGTGGCA CAAGTGGCTG  100
CTATTGCTGT TAGGGACAAA AGTGCAAATG GTGTTAAAGT TGAACTTTCT  150
GAAGAGGCAA GAGCTGGTGT TAAAGCTAGT AGTGATTGGG TGATGGATAG  200
ATGGATAGTA CGAACAAGCT TGCATGGAAT TCGAAGGGAG TGATTGGGTG  250
ATGGATAGTA T                     ◀────────────────── 261
───────────                           PAL-R127
```

FIG. 2D

```
ATCAAATTCGAAATCTTGGAAGCCATCACCACTTTCCTTAACCACAACAT    50
CACCCCATGCTTGCCTCTTCGCGGTACAATCACTGCCTCTGGTGATCTTG   100
TCCCCTTGTCCTACATTGCCGGTTTACTAACCGGCCGCCCCAACTCCAAG   150
GCCGTTGGACCCAACGGAGAAGCTCTCAACGCCGAAGAAGCATTTCGCCT   200
TGCTGGCCTCAGCGGTGGCTTTTTCCAGCTGCAGCCTAAAGAAGGCCTTG   250
CTCTTGTTAACGGAACAGCAGTTGGTTCTGGCTTGGCCTCTATTGTTCTA   300
TTTGAAGCTAACGTGCTTGCTGTCTTATCTGTAGTGCTGTCAGCAATCTT   350
TGCTGAAGTGATGAATGGCAAGCCCGAGTTCACCGATCATTTGACGCATA   400
AGTTGAAGCACCATCCCGGCCAAATTGAGGCCGCGGCTATCATGGAACAT   450
ATCTTGGATGGAAGCTCTTACGTCAAGGCTGCTCAAAAGTTGCATGAGTT   500
GGATCCCCTGCAAAAGCCAAAGCTGGACCGATACGCTCTCAGGACATCTC   550
CGCAGTGGCTGGGTCCACAAATCGAAGTTATTCGCGCAGCAACAAAAATG   600
ATTGAAAAGGAGATCAATTCAGTTAATGATAACCCTCTCATTGATGTGTC   650
CAGGAACAAGGCCTAACATGGCGGCAACTTCCAGGGCACCCCCATTGGAG   700
TGAGCATGGACAACGCTCGACTGGCCATTGCATCTATCGGCAAACTGATG   750
TTTGCTCAATTTTCCGAGCTTGTTAATGAATTACTACAACAATGGGTTGC   800
CCGTCCAATCTTTCTGGAGGAAGGAATCCAAGTTTGGACTATGGATTCA   850
AGGGAGCTGAGATTGCTATGGCTGCATACTGTTCTGAACTCCAGTATTTG   900
GGCAATCCAGTGACCAACCATGTCCAGAGTGCCGAGCAACACAACCAAGA   950
CGTCAACTCCTTGGGATTAATCTCTTCAAGAAAAACGGCAGAAGCCATTG  1000
ATATCTTGAAGCTCATGTCATCCACTTATTTGGTGGCTCTTTGTCAAGCA  1050
ATCGATTTGAGGTTTTTGGAAGAAAACTTGAAAAATGCTGTTAAGAATAT  1100
TGTCAGCCAAGTGGCAAAGCGAACTCTGACAATGGGCGCTAATGGAGAAC  1150
TGCATCCTTCACGGTTTTGTGAGAAGGATTTGCTCAGAGTGGTGGACCGC  1200
GAATACGCCTTTGCCTATGTGGATGACCCTTGCAGCGCTACCTATCCATT  1250
AATGCAAAAGTTAAGGCAAGTGCTCGTGGATCATGCGTTGAAGAATGGTG  1300
ATCAGGAGGGG                                         1311
```

*FIG. 3*

AAAAGTTGTAGCGGGAGGGC TGGACGATGCGTGGAGCGGAAAATGCTGGA  50

GTATTGGACCACCAACCAAACAAAATAGTTTTAGTATATGGGGTTTCGAA  100

CTTTCCAGTCAACCTACAACAATCTGCTTCTATAAACAATAATAAAAGAG  150

TAATTAAATTACTGGTAGCGTTGGTGTATTTGGATTTGCCAGCTTTGCTT  200

CCAAACTCATATCATCAATTGATAGCACTTGGATACGGAGATCGCTTTT  250
                  CAAT Box

GTCTGCCTTAGTATGATATGATTGCTCACCCGCTGTAGACATGATTTAAA  300

GGAAAATAACACAAATATATATATATAAGACCAACAAATTATAACTGAAA  350
                  TATA Box

ACTTTTCAGTAATGTTAATTCTAACACATGTGACTAGACCTGCTATCATC  400
                            Potential ORF
AGCTGCAATTCTAGAGGAAACTTGGACCAGATCAGAAGTTGTAAAGGGCT  450

GCAGTCCATTCCTGCACTATTCAGTTTGCAGGTAGATGGGTGGACCATTA  500

TATGGATCTGGTCCAGCGTGAATGCAGTTGTAGTAAAGACATGTTGGATT  550

TGTTATGGATCAAACTACTACTAGTAGGGAAATGCTTCAAAGACTTCTCT  600

TGTGATTTTCTCCCAGCCGAATGGTCCAAGTACACTAGCAAAAGAAGCAC  650

AAACGGTACCAATGACTCGAGCGAGCTGACATTTTGGGCTTCAGATTAGC  700

ACAAGACAAAAGGATTTTTCACTTTTCTTCTGTAGGTGATCCTGGACTCG  750

CAGGTTGGCATGCTCAATTCAGGAGCTTTTGAGATTGGATAGGGTGTTGG  800

TTATGAATGCACCGCAGGTTGCATGCTCAATTCAGAGCCCTTCACATGTA  850

ACCGTGTGTAGCCCAGGCCCAAATGCCCCGGAAGTTTAAACTGAAATCTC  900

FIG. 5A

```
GGAAGAGCAG ATGGCAACGG TCGTAATTCG TCAAGCAATC CGAAACGTCG CCACACCCCC    960

ACGCCAGCTG GAAAATCAGT TCAAAATTCA AAATTCATTT TGGAGCCGTT CAAACAAAAT   1020

TGTTTCAGTT TTGCCCCTCG CCTGCTGCCC TAATCTTACC CCGCCATTGG GGCTTGGATT   1080

ACTCGCTCCA GTCTATATAT ATAACTCCCT CCCGCATTGC CTCACCACAC GACCCCAAGT   1140

CCTCTCCTTC TTCTCCTTTC CCAGATCTCG GAGGTCTCTC ACTCTTCCGA TCCAGAGACG   1200

TCTTTGTATA CGCCTCTGGT ATCTCCATTC CTCCTTTTTC CCTCTCTTCC AAAAATCTCC   1260

TATTCATTTC TCAAAACATC GCGAAAATGA GAGAGTGCAT CTCCATCCAT ATTGGTCAGG   1320

CCGGTATCCA GGTCGGAAAT GCCTGCTGGG AGCTCTACTG CCTCGAGCAC GGCATCCAGG   1380

TAAATTGCCT TCTATCTAAC CTCTTATATT TCAGATCTGC TGTTTCTCTC ATTTTTGTTC   1440

AAGGAAATGA TTCATCTTTG GTTTGATTTT GGGTGTTGTG GAATAGCCTG ATGGACAAAT   1500

GCCGAGCGAC CACACCGTCG GAGGCGGAGA CGACGCTTTC AACACCTTCT TCAGCGAAAC   1560

CGGAGCCGGC AAACACGTTC CTCGTGCCGT GTTCGTCGAT CTGGAGCCCA CTGTCATCGA   1620

TGAAGTCCGA ACCGGCACCT ACCGCCAACT CTTCCACCCT GAGCAGCTCA T            1671
```

FIG. 5B

```
CATTTCTTGCCAGAAAGCACTAGTGAATATTCTATCCCTGTCAGTCACTA      50
TAGATTCTGGAAGTCCATGTAATCTAAAAATGTTTCCAGGAAGAGTTGAG      100
CCACCTGTTTGGTTGTGAAGGGGTGAGCTAAGGCAAGCAAATGACCTACT      150
TTGGACAACCTATCAATCACCACCATCACTGTATTATATCCTTGAGATTC      200
TGGAAGGCTCTCTATGAAGTCCATGGTTAGGTGAGTCCAAGCTAAACGAG      250
GAATAGGTGATGGTTGTAGCAGTCCAAGGTAGGGTCCATGCTTTGACTTA      300
AATCTTTGGCATATGTCACAAGCATGAATATACCTGATGATTTTCCCCAA      350
              SBF-1
ATGTTTTTGAG[GTTTTTAATA]CCGGGAATGGCCCAGGAAAAAGGGCCCTG     400
GCTTTGCACCAAGGTCCCCTAAGAATTTCTGGCAAAAGTTCAAGCGGTTC      450
CAAAGTGCCCCAATGGGACCTCTCCAAAAAAGGTGCCCCGGGGACAAGTT      500
GTGCTCAGTTCGGCGCGTTTCAAGACAGGTTTTGGCCAGAAAGCAAAGGG      550
GTTCCAAAGGGTGTCAGAGGGTCCATGTTTCAAAACTCCGGGTGTCTTGG      600
TCCCCCATAATTGACTTCGGCTAAGTAAAGGAAAACCTTAGCCGAGGCTG      650
                                           B-myb
TAATTAAGCCGAAGTCCTAACGCGATGGCGAACGGCCGAG[GTGGTCGGA]G    700
              B-myb
CCTAAGAGACATAGGCGGGACCCCAGCTCT[GCCGACCTG]GAAATACCCTC    750
TATABox
[CTCATATACCATTAC]TAGTTAGTAGTCACCACTGCTACTGCTTCAGTTCC    800
TTTTATCACTTGCTTTACATGAATTAAGTCGATGCTCTTCCTTGAATAAC      850
TAGCGATTAGTTTCGTGGTGACCTATCTAGCCATTTTTCTGTTTGGGTGG      900
CATCAATCCTGAACACAGAAAGCTGCAAGATGGAACATGGTCATGACGAA      950
                                  [Exon1         ]
GGCGTGAAAGTCTCGGAGTTTTGCTTGAAACCAGATCCTCTGAACTGGGG      1000
[                                                 ]
AGTGGCAGCTGAGTCACTGATGGGAAGTCATTTGGACGAAGTGAAGCGCA      1050
[                                                 ]
TCGTAGCTGAGTTTAGGAAGCCGGTGGTAAAGCTCGGCGGTGAGAGCTTG      1100
[                                                 ]
ACCGTTGCTCAGGTGGCCGCGATTGCCGCCAAAGGTGATCAGGGTGTGAA      1150
[                                                 ]
GGTGGAGCTGGCGGAGGACGCAAGGGCTGGGGTGAAGGCAAGCACCGACT      1200
[                                                 ]
GGGTGATGGAGAGTATGAACAAAGGCACTGATAGTTACGGAGTTACCACT      1250
[                                                 ]
GGGTTTGGTGCCACTTCACACAGGCGGACCAATCAAGGCGGTGCCCTTCA      1300
[                                                 ]
GAAGGAGCTTATTAGGTAAATTAGCTTTAGCTTCATCCTTAAATTTTGCC      1350
[        ]
```

*FIG. 6A*

```
TCTGCATTTTTACCACTTTCAAGTTCTTTTTTGTTTTTTGCGTTAATGGT  1400
GGCCACAATTTTACTGTGCTGGGATCGGGCTCATGCATTTAACCTGGATG  1450
ATAAACTACCTGTTTGAATTTGTTTCTGAAAAACTCCACTATTTCCCCCA  1500
AAAAAAGCTTGATGGAATTCGCTGCTGAGTCAATGAAAGGCCAACTGACG  1550
ACGAAATCTGACATCTATAGTTTTGGGGTGGTCTTGTTGGAGATCATCAC  1600
AGGAAGGAGAGCCATCGATAATACAAGGCCTACAGCAGAGCAGAACCTGA  1650
TTTCTTGGGTTAGTTTCTGGACTTGCTATTTTTGAATTGACTAAAGAAGC  1700
TTCGGCACTTATTTCTATAACTTAAAGAACCAGTAACCAAGCCATCTTTC  1750
GTTCTGAGATACCTTAATGTTCATTTGGATAATTGGATGCAAGATTTTTT  1800
TGGGTTCAGTATTCTGCACTAACAATTTGAAAGTCGAAAGGCAAATATTC  1850
TACACGTCTGTCTGCAGGAGTAATCATGTCAATTGGAGTAATAGCTATAC  1900
TATACTATGGTACTTGACAAGAAACGTTTCAATATAGTTTATTTGTATAA  1950
ATTTTAATTGTCATGTTGAATACATGTGCAAGGCACATGCATTTTCCTAG  2000
TTCATGTAAAATGGGGTAATAGCTATACTATGGTACTTACCAAGAAATGT  2050
TTCCCAACAATGTAGTTGGTTTTAACATTCTTTGATTGTCATTTANTTTG  2100
CCCATGATTTTGTTCTCATTCTTGCAGGCAAAACCTTATTTTAAAGACAG  2150
AAGACAATTTACATTCCTGGCTGACCTTTGCTGGAANGGGATTACCCTGT  2200
AAAAGCTTGATGGCCGGGATGGTGCTTCAACTTATGCGTCAAATGATCGG  2250
TGAACTCGGGTTTGCCATTCATCACTTCAGCAAAGATTGCTGACAGCACT  2300
ACAGATAAGACAGCAAGCACGTTAGCCTCAAATAGAACAATAGAGGCCAA  2350
GCCAGAACCAACAGCTGTTCCGTTAACAAGAGCAAGGCCTTCTTTAGGCT  2400
GCAGCTCGAAAAAGCCACCGCTGAGGCCAGCAATGCGAAATGCTTCTTCG  2450
GCGTTTAGAGCTTCTCCGTTGGGTCCAACGGCCTTGGAGTTGGGGCGGCC  2500
AGTTAGTAAACCGGCAATGTAGGACAAGGGGACAAGATCACCAGAGGCAG  2550
TGATTGTACCGCGAAGAGGCAAGCATGGGGTGATGTTGTGGTTAAGGAAA  2600
GTGGTGATGGCTTCCAAGATTTCGAATCTGATCCCGGAATAACCTTGAAG  2650
AAGGGTGTTGATTCTTACAAGCACCGCTGCCCTTGTTGCTGGGTGTGGCA  2700
GCGTGTGGCAAGTTTCCGTGCCGTTTCCGAAGATTCCCGCGTTCAGAAAT  2750
CTGTCAATTTACACAATAATCCATGTATGTCAGGATCATTCTCCTTTCTA  2800
TTCCCTGCACCCGACTCTACAGATTCGTTCGTTTTGACAAAGTATTCCA  2850
TTTGTTTCCGATGGATGAACGGGCAACCATAAAAAGGAAAAAGGGGAGGA  2900
GGGGGAAGATGAGGTAGGTATTAGGAGGCAAATGGGAAGCCAACAAAAAA  2950
AAAATTTCAAAGCAAAATTGAGGAAATTAAACAAAGGGTACTACAATATT  3000
```

*FIG. 6B*

```
TAACCTTTTCACTTGTCCCTATTTGTCTTATTTAAAACAGTGTATGGTTG      3050
CCCGCTGATCCATCGGAAACAAATGGAAAATTAAAAAAACGAACGGATCT      3100
GTAGAGTCGGGTGCAGGGAATAGAAAGGAGAATGATCCTGACATGCATGG      3150
ATTATTGTGTAAATTGACAGATTTCTGAACGCGGGAATGTTCGGAAACGG      3200
                            Exon2
CACGGAAACTTGCCACATGGGCCACAGTCAGCAACAAGGGCAGCGATGC       3250

TTGTAAGAATCAACACCCTTCTTCAAGGTTATTCCGGGATCAGATTCGAA      3300

ATCTTGGAAGCCATCACCACTTTCCTTAACCACAACATCACCCCATGCTT      3350

GCCTCTTCGCGGTACAATCACTGCCTCTGGTGATCTTGTCCCCTTGTCCT      3400

ACATTGCCGGTTTACTAACCGGCCGCCCCAACTCCAAGGCCGTTGGACCC      3450

AACGGAGAAGCTCTAAACGCCGAAGAAGCACTTCGCCTTGCTGGCCTCAG      3500

CGGTGGCTTTTTCGAGCTGCAGCCTAAAGAAGGCCTTGCTCTTGTTAACG      3550

GAACAGCAGTTGGTTCTGGCTTGGCCTCTATTGTTCTATTTGAAGCTAAC      3600

GTGCTTGCTGTCTTATCTGTAGTGCTGTCAGCAATCTTTGCTGCCGTGAT      3650

GACTGGCAAGCCCGAGTTCACCGATCATTTGACGCATAAGTTGAAGCACC      3700

ATCCCGGCC                                               3709
```

*FIG. 6C*

SEQUENCE LISTING

<160> NUMBER OF SEQ ID NOS: 52

<210> SEQ ID NO 1
<211> LENGTH: 1671
<212> TYPE: DNA
<213> ORGANISM: Coffea arabica

<400> SEQUENCE: 1

```
aaaagttgta gcgggagggc tggacgatgc gtggagcgga aaatgctgga gtattggacc      60
accaaccaaa caaaatagtt ttagtatatg gggtttcgaa ctttccagtc aacctacaac     120
aatctgcttc tataaacaat aataaaagag taattaaatt actggtagcg ttggtgtatt     180
tggatttgcc agctttgctt ccaaactcat atcatcaatt tgatagcact tggatacgga     240
```

```
gatcgctttt gtctgcctta gtatgatatg attgctcacc cgctgtagac atgatttaaa        300
ggaaaataac acaaatatat atatataaga ccaacaaatt ataactgaaa acttttcagt        360
aatgttaatt ctaacacatg tgactagacc tgctatcatc agctgcaatt ctagaggaaa        420
cttggaccag atcagaagtt gtaaagggct gcagtccatt cctgcactat tcagtttgca        480
ggtagatggg tggaccatta tatgatctg gtccagcgtg aatgcagttg tagtaaagac         540
atgttggatt tgttatggat caaactacta ctagtaggga aatgcttcaa agacttctct        600
tgtgattttc tcccagccga atggtccaag tacactagca aaagaagcac aaacggtacc        660
aatgactcga gcgagctgac atttgggct tcagattagc acaagacaaa aggattttc          720 acttttcttc tgtaggtgat cctggactcg caggttggca tgctcaattc aggagctttt       780
gagattggat agggtgttgg ttatgaatgc accgcaggtt gcatgctcaa ttcagagccc       840
ttcacatgta accgtgtgta gcccaggccc aaatgccccg aagtttaaa ctgaaatctc         900 ggaagagcag atgcaacgg tcgtaattcg tcaagcaatc cgaaacgtcg ccacaccccc        960
acgccagctg gaaatcagt tcaaaattca aaattcattt tggagccgtt caaacaaaat        1020
tgtttcagtt ttgcccctcg cctgctgccc taatcttacc ccgccattgg ggcttggatt       1080
actcgctcca gtctatatat ataactccct cccgcattgc ctcaccacac gaccccaagt       1140
cctctccttc ttctccttc ccagatctcg gaggtctctc actcttccga tccagagacg       1200
tctttgtata cgcctctggt atctccattc ctcctttttc cctctcttcc aaaaatctcc      1260
tattcatttc tcaaaacatc gcgaaaatga gagagtgcat ctccatccat attggtcagg      1320
ccggtatcca ggtcggaaat gcctgctggg agctctactg cctcgagcac ggcatccagg      1380
taaattgcct tctatctaac ctcttatatt tcagatctgc tgtttctctc atttttgttc     1440
aaggaaatga ttcatctttg gtttgatttt gggtgttgtg aatagcctg atggacaaat       1500 gccgagcgac cacccgtcg gaggcggaga cgacgctttc aacaccttct tcagcgaaac      1560
cggagccggc aaacacgttc ctcgtgccgt gttcgtcgat ctggagccca ctgtcatcga     1620
tgaagtccga accggcacct accgccaact cttccaccct gagcagctca t                1671

<210> SEQ ID NO 2
<211> LENGTH: 929
<212> TYPE: DNA
<213> ORGANISM: Coffea arabica

<400> SEQUENCE: 2
catttcttgc cagaaagcac tagtgaatat tctatccctg tcagtcacta tagattctgg        60
aagtccatgt aatctaaaaa tgtttccagg aagagttgag ccacctgttt ggttgtgaag       120
gggtgagcta aggcaagcaa atgacctact ttggacaacc tatcaatcac caccatcact       180
gtattatatc cttgagattc tggaaggctc tctatgaagt ccatggttag gtgagtccaa       240
gctaaacgag gaataggtga tggttgtagc agtccaaggt agggtccatg ctttgactta       300
aatctttggc atatgtcaca agcatgaata tacctgatga ttttcccaa atgttttga        360 ggttttaat accgggaatg gcccaggaaa aagggccctg gctttgcacc aaggtcccct        420
aagaatttct ggcaaaagtt caagcggttc caaagtgccc caatgggacc tctccaaaaa      480
aggtgccccg gggacaagtt gtgctcagtt cggcgcgttt caagacaggt tttggccaga      540
aagcaaaggg gttccaaagg gtgtcagagg gtccatgttt caaaactccg ggtgtcttgg      600 tccccccataa ttgacttcgg ctaagtaaag gaaaacctta gccgaggctg taattaagcc       660
gaagtcctaa cgcgatggcg aacggccgag gtggtcggag cctaagagac ataggcggga       720
```

-continued

```
ccccagctct gccgacctgg aaatacccctc ctcatatacc attactagtt agtagtcacc    780
actgctactg ctttcagttcc tttttatcact tgctttacat gaattaagtc gatgctcttc    840
cttgaataac tagcgattag tttcgtggtg acctatctag ccattttcct gtttgggtgg     900
catcaatcct gaacacagaa agctgcaag                                       929
```

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 3

```
ggaattcggt atccaggtcg gaaac                                            25
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 4

```
ggaattcgtg ctgggagctc tactg                                            25
```

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 5

```
gcaagcttac agtgggttca agatcaac                                         28
```

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 6

```
gcaagcttat gagctgctca gggtgg                                           26
```

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 7

```
ggaattcgct gctgagtcaa tgaaagg                                          27
```

<210> SEQ ID NO 8
<211> LENGTH: 27
<212> TYPE: DNA
<213> ORGANISM: Artificial Sequence

```
<220> FEATURE:
<223> OTHER INFORMATION: Description of Artificial Sequence: Synthetic
      Oligonucleotide Primer

<400> SEQUENCE: 8
ggaattcgaa agggagtcat ttggatg                                            27

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 9
gcaagcttat actatccatc acccaatcac                                         30

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 10
gcaagcttgt tcatactatc catcaccc                                           28

<210> SEQ ID NO 11
<211> LENGTH: 638
<212> TYPE: DNA
<213> ORGANISM: Artificial Sequence
<220> FEATURE:
<221> NAME/KEY: unsure
<222> LOCATION: (2)
<223> OTHER INFORMATION: N at any position in this sequence  is
      either A, C, G, or T.
<220> FEATURE:
<223> OTHER INFORMATION: Description of Artificial Sequence:
      Alpha Tubulin Consensus Sequence

<400> SEQUENCE: 11
gnnnnnnnnn nnccntngtn ntngcctctc cccgagcaca nnnnctnncc ggcnnccnng        60 cccnanncen nngtntcggc ggcngcncag ccncagccgc ccgnccaaga tgagggagtg       120
catctcgatc cacatcggcc aggccgggat ccaggtcggc aacgcgtgct gggagctcta       180
ctgcctcgag catggcatcc agcctgatgg ccagatgccc agtgacaaga ccgttggggg       240
aggagatgat gcgttcaaca ccttcttcag tgagactggt gctggcaagc acgtgcccag       300
ggccgtcttt gtcgatcttg agcccactgt cattgatgag gtgcggactg gtgcctaccg       360
ccagctcttc caccctgagc agctcatcag tggcaaggag gatgcagcca acaactttgc       420
ccgtggccac tacaccattg gcaaggagat tgttgatctg tgcctggacc gtatccgcaa       480
gcttgcagac aactgcactg ggctgcaggg attccttgtg ttcaatgctg ttggtggtgg       540
aactggctct ggacttggtt ctcttctgtt ggagcgtctc tctgttgatt atggaaagaa       600
gtccaagctt gggnttcacc gtgtacccett ccccacag                              638

<210> SEQ ID NO 12
<211> LENGTH: 500
<212> TYPE: DNA
<213> ORGANISM: Artificial Sequence
```

```
<220> FEATURE:
<221> NAME/KEY: unsure
<222> LOCATION: (6)
<223> OTHER INFORMATION: N at any position in this sequence is either
      A, C, G, or T.
<220> FEATURE:
<223> OTHER INFORMATION: Description of Artificial Sequence:
      Phenylaninine Ammonia Lyase Consensus Sequence

<400> SEQUENCE: 12
gatccnttga actgggnnnt ggcngcngag ncattgaang gnagncantt ggatgaagtg     60
aagngnatgg tggcngagtt naggaagccg gtngtgaagc ttggaggnga gacnttgacg    120
atntctcagg tggcngcnta ttgcngccan nnatgatgnt nnnnnngtca ngtggagct    180 ntcngaggcg gcnagngctg gcgttaaggc nagcagtgat tgggtgatgg atagtatgaa   240
caaagggact gatagctatg gtgtcactac tggctttcgt gctacttctc acaggagaac   300
caagcaaggt ggtgctcttc agaaggagct cattaggttc ttgaatgctg gaatatttgg   360
caatggaaca gagtcaagtc acacattgcc acactcagct acaagggcag ctatgcttgt   420
gagaatcaac actctcctcc aaggatactc tggcatcaga tttgaaatct tggaagccat   480
taccaaattc cttaaccaca                                                500

<210> SEQ ID NO 13
<211> LENGTH: 203
<212> TYPE: DNA
<213> ORGANISM: Nicotiana tabacum

<400> SEQUENCE: 13
aaagggagtc atttggatga agtgaaaaaa atggtgagtg aatttagaaa accagtggta    60
aaacttggtg gtgaaacttt aacagtggca caagtggctg ctattgctgt tagggacaaa   120
agtgcaaatg gtgttaaagt tgaactttct gaagaggcaa gagctggtgt taaagctagt   180
agtgattggg tgatggatag tat                                           203

<210> SEQ ID NO 14
<211> LENGTH: 261
<212> TYPE: DNA
<213> ORGANISM: Coffea arabica

<400> SEQUENCE: 14
aaagggagtc atttggatga agtgaaaaaa atggtgagtg aatttagaaa accagtggta    60
aaacttggtg gtgagacttt aacagtggca caagtggctg ctattgctgt tagggacaaa   120
agtgcaaatg gtgttaaagt tgaactttct gaagaggcaa gagctggtgt taaagctagt   180
agtgattggg tgatggatag atggatagta cgaacaagct tgcatggaat tcgaagggag   240
tgattgggtg atggatagta t                                             261

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:  Synthetic
      Oligonucleotide Primer

<400> SEQUENCE: 15
caatgaacac ccttagtgat g                                              21
```

```
<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 16
aactttctga agaggcaaga gc                                              22

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 17
cgggatcctc cctgtaaatt tgatgg                                          26

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 18
caatagcagc cacttgtgcc                                                 20

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 19
gcaagcttca agacagtaaa gctcc                                           25

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 20
gtggctgcta ttgctgttag g                                               21

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 21
ggaattcgga aacgcttgct gggagc                                          26
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 22
catttgtcca tcaggctatt                                              20

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 23
gcaagcttcg aattgggaac gaaggaacc                                    29

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 24
cacaacaccc aaaatcaaac c                                            21

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 25
actctagaag agttagctgc atgcagg                                      27

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 26
ctaccgccaa ctcttccacc                                              20

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide Primer
<220> FEATURE:
<221> NAME/KEY: unsure
<222> LOCATION: (5)
<223> OTHER INFORMATION: N at any position in this sequence is either
      A, C, G, or T.

```
<400> SEQUENCE: 27
atggnttcca tgtncatgc                                                  19

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 28
caatagcagc cacttgtgcc                                                 20

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 29
ggaattcggt atccaggtcg gaaac                                           25

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 30
tttttgtttg ttgtgggggt gt                                              22

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 31
gagttggagg tagggtgcc                                                  19

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 32
caaagccgcc gaagtgat                                                   18

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide Primer
```

```
<400> SEQUENCE: 33
agcagccact tgtgccactg                                              20

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 34
cccaagcttc gcttttgtct gccttagtat g                                 31

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 35
cgggatcctc tcattttcgc gatgttttga g                                 31

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 36
gccggggcga gaccatagg                                               19

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 37
cgcacgcgca aggaacc                                                 17

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 38
tagcgggact ttgcaagtg                                               19

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide Primer
```

<400> SEQUENCE: 39
cagcagcagt tcatcaatc a 21

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
Oligonucleotide Primer

<400> SEQUENCE: 40
cccactatcc ttcgcaagac cc 22

<210> SEQ ID NO 41
<211> LENGTH: 330
<212> TYPE: DNA
<213> ORGANISM: Coffea arabica

<400> SEQUENCE: 41

```
cctgctggga gctctactgc ctcgagcacg gcatccaggt aaattgtctt ctatctaacc    60
tcttatattt cagatctgct gtttctctca tttttgttca aggaaatgat tcatctttgg   120
tttgattttg ggtgttgtgg aatagcctga tggacaaatg ccgagcgacc acaccgtcgg   180
aggcggagac gacgctttca acacttctt cagcgaaacc ggagccggca aacacgttcc   240
tcgtgccgtg ttcgtcgatc tggagcccac tgtcatcgat gaagtccgaa ccggcaccta   300
ccgccaactc ttccaccctg agcagctcat                                    330
```

<210> SEQ ID NO 42
<211> LENGTH: 290
<212> TYPE: DNA
<213> ORGANISM: Nicotiana tabacum

<400> SEQUENCE: 42

```
gtatccaggt cggaaacgcc tgctgggagc tctactgcct cgagcacggc atccaggtaa    60
attgccttct atctaacctc tatatttcag atctgctgtt tctctcattt ttgttcaagg   120
aaatgattca tctttggttt gattttgggt gttgtggaat agcctgatgg acaaatgccg   180
agcgaccaca ccgtcggcgg cggagacgac gctttcaaca ccttcttcag cgaaaccgga   240
gccggcaaac acgttcctcg tgccgtgttc gttgatcttg aacccactgt               290
```

<210> SEQ ID NO 43
<211> LENGTH: 1311
<212> TYPE: DNA
<213> ORGANISM: Coffea arabica

<400> SEQUENCE: 43

```
atcaaattcg aaatcttgga agccatcacc actttcctta accacaacat caccccatgc    60
ttgcctcttc gcggtacaat cactgcctct ggtgatcttg tccccttgtc ctacattgcc   120
ggtttactaa ccgccgccc caactccaag gccgttggac ccaacggaga agctctcaac   180
gccgaagaag catttcgcct tgctggcctc agcggtggct ttttccagct gcagcctaaa   240
gaaggccttg ctcttgttaa cggaacagca gttggtctg gcttggcctc tattgttcta   300
tttgaagcta acgtgcttgc tgtcttatct gtagtgctgt cagcaatctt tgctgaagtg   360
atgaatggca agcccgagtt caccgatcat ttgacgcata agttgaagca ccatcccggc   420
caaattgagg ccgcggctat catggaacat atcttggatg gaagctctta cgtcaaggct   480
```

```
gctcaaaagt tgcatgagtt ggatcccctg caaaagccaa agctggaccg atacgctctc      540
aggacatctc cgcagtggct gggtccacaa atcgaagtta ttcgcgcagc aacaaaaatg      600
attgaaaagg agatcaattc agttaatgat aaccctctca ttgatgtgtc caggaacaag      660
gcctaacatg gcggcaactt ccagggcacc cccattggag tgagcatgga caacgctcga      720
ctggccattg catctatcgg caaactgatg tttgctcaat tttccgagct tgttaatgaa      780
ttactacaac aatgggttgc ccgtccaatc ttttctggag aaggaatcc  aagtttggac      840 tatggattca agggagctga gattgctatg ctgcatact  gttctgaact ccagtatttg      900
ggcaatccag tgaccaacca tgtccagagt gccgagcaac acaaccaaga cgtcaactcc      960
ttgggattaa tctcttcaag aaaaacggca gaagccattg atatcttgaa gctcatgtca     1020
tccacttatt tggtggctct tgtcaagca  atcgattgga ggttttgga  agaaaacttg     1080 aaaaatgctg ttaagaatat tgtcagccaa gtggcaaagc gaactctgac aatgggcgct     1140
aatggagaac tgcatccttc acggttttgt gagaaggatt tgctcagagt ggtggaccgc     1200
gaatacgcct ttgcctatgt ggatgaccct tgcagcgcta cctatccatt aatgcaaaag     1260
ttaaggcaag tgctcgtgga tcatgcgttg aagaatggtg atcaggaggg g              1311
```

<210> SEQ ID NO 44
<211> LENGTH: 3709
<212> TYPE: DNA
<213> ORGANISM: Coffea arabica
<220> FEATURE:
<221> NAME/KEY: unsure
<222> LOCATION: (2096)
<223> OTHER INFORMATION: N at position 2096 is unknown
<220> FEATURE:
<221> NAME/KEY: unsure
<222> LOCATION: (2187)
<223> OTHER INFORMATION: N at position 2187 is unknown

<400> SEQUENCE: 44

```
catttcttgc cagaaagcac tagtgaatat tctatccctg tcagtcacta tagattctgg       60
aagtccatgt aatctaaaaa tgtttccagg aagagttgag ccacctgttt ggttgtgaag      120
gggtgagcta aggcaagcaa atgacctact ttggacaacc tatcaatcac caccatcact      180
gtattatatc cttgagattc tggaaggctc tctatgaagt ccatggttag gtgagtccaa      240
gctaaacgag gaataggtga tggttgtagc agtccaaggt agggtccatg ctttgactta      300
aatctttggc atatgtcaca agcatgaata tacctgatga ttttcccccaa atgttttga    360 ggttttttaat accgggaatg gcccaggaaa aagggccctg gctttgcacc aaggtccct     420 aagaatttct ggcaaaagtt caagcggttc caaagtgccc caatgggacc tctccaaaaa     480
aggtgccccg gggacaagtt gtgctcagtt cggcgcgttt caagacaggt tttggccaga     540
aagcaaaggg gttccaaagg gtgtcagagg gtccatgttt caaaactccg ggtgtcttgg     600
tcccccataa ttgacttcgg ctaagtaaag gaaaaccttta gccgaggctg taattaagcc     660
gaagtcctaa cgcgatggcg aacggccgag tggtcggag  cctaagagac ataggcggga     720
ccccagctct gccgacctgg aaatacccctc ctcatatacc attactagtt agtagtcacc     780
actgctactg cttcagttcc ttttatcact tgctttacat gaattaagtc gatgctcttc     840
cttgaataac tagcgattag tttcgtggtg acctatctag ccattttct  gtttgggtgg     900 catcaatcct gaacacagaa agctgcaaga tggaacatgg tcatgacgaa ggcgtgaaag     960
tctcggagtt ttgcttgaaa ccagatcctc tgaactgggg agtggcagct gagtcactga    1020
tgggaagtca tttggacgaa gtgaagcgca tcgtagctga gtttaggaag ccggtggtaa    1080
```

```
agctcggcgg tgagagcttg accgttgctc aggtggccgc gattgccgcc aaaggtgatc    1140
agggtgtgaa ggtggagctg gcggaggacg caagggctgg ggtgaaggca agcaccgact    1200
gggtgatgga gagtatgaac aaaggcactg atagttacgg agttaccact gggtttggtg    1260
ccacttcaca caggcggacc aatcaaggcg gtgcccttca gaaggagctt attaggtaaa    1320
ttagctttag cttcatcctt aaattttgcc tctgcatttt taccactttc aagttctttt    1380
ttgttttttg cgttaatggt ggccacaatt ttactgtgct gggatcgggc tcatgcattt    1440
aacctggatg ataaactacc tgtttgaatt tgtttctgaa aaactccact atttccccca    1500
aaaaaagctt gatggaattc gctgctgagt caatgaaagg ccaactgacg acgaaatctg    1560
acatctatag ttttggggtg gtcttgttgg agatcatcac aggaaggaga gccatcgata    1620
atacaaggcc tacagcagag cagaacctga tttcttgggt tagtttctgg acttgctatt    1680
tttgaattga ctaaagaagc ttcggcactt atttctataa cttaaagaac cagtaaccaa    1740
gccatctttc gttctgagat accttaatgt tcatttggat aattggatgc aagatttttt    1800
tgggttcagt attctgcact aacaatttga agtcgaaag gcaaatattc tacacgtctg    1860
tctgcaggag taatcatgtc aattggagta atagctatac tatactatgg tacttgacaa    1920
gaaacgtttc aatatagttt atttgtataa attttaattg tcatgttgaa tacatgtgca    1980
aggcacatgc attttcctag ttcatgtaaa atggggtaat agctatacta tggtacttac    2040
caagaaatgt ttcccaacaa tgtagttggt tttaacattc tttgattgtc atttantttg    2100
cccatgattt tgttctcatt cttgcaggca aaaccttatt ttaaagacag aagacaattt    2160
acattcctgg ctgacctttg ctggaanggg attaccctgt aaaagcttga tggccgggat    2220
ggtgcttcaa cttatgcgtc aaatgatcgg tgaactcggg tttgccattc atcacttcag    2280
caaagattgc tgacagcact acagataaga cagcaagcac gttagcctca aatagaacaa    2340
tagaggccaa gccagaacca acagctgttc cgttaacaag agcaaggcct tctttaggct    2400
gcagctcgaa aaagccaccg ctgaggccag caatgcgaaa tgcttcttcg gcgtttagag    2460
cttctccgtt gggtccaacg gccttggagt tggggcggcc agttagtaaa ccggcaatgt    2520
aggacaaggg gacaagatca ccagaggcag tgattgtacc gcgaagaggc aagcatgggg    2580
tgatgttgtg gttaaggaaa gtggtgatgg cttccaagat ttcgaatctg atcccggaat    2640
aaccttgaag aagggtgttg attcttacaa gcaccgctgc ccttgttgct gggtgtggca    2700
gcgtgtggca agtttccgtg ccgtttccga agattcccgc gttcagaaat ctgtcaattt    2760
acacaataat ccatgtatgt caggatcatt ctcctttcta ttccctgcac ccgactctac    2820
agattcgttc gttttgacaa aagtattcca tttgtttccg atggatgaac gggcaaccat    2880
aaaaaggaaa aaggggagga gggggaagat gaggtaggta ttaggaggca aatgggaagc    2940
caacaaaaaa aaatttcaa agcaaaattg aggaaattaa acaaagggta ctacaatatt    3000 taacctttc acttgtccct attttgtctta ttttaaacag tgtatggttg cccgctgatc    3060
catcggaaac aaatggaaaa ttaaaaaaac gaacggatct gtagagtcgg gtgcagggaa    3120
tagaaaggag aatgatcctg acatgcatgg attattgtgt aaattgacag atttctgaac    3180
gcgggaatgt tcggaaacgg cacggaaact tgccacatgg ggccacagtc agcaacaagg    3240
gcagcgatgc ttgtaagaat caacacccct cttcaaggtt attccgggat cagattcgaa    3300
atcttggaag ccatcaccac tttccttaac cacaacatca ccccatgctt gcctcttcgc    3360
ggtacaatca ctgcctctgg tgatcttgtc cccttgtcct acattgccgg tttactaacc    3420
ggccgcccca actccaaggc cgttggaccc aacggagaag ctctaaacgc cgaagaagca    3480
```

-continued

```
cttcgccttg ctggcctcag cggtggcttt ttcgagctgc agcctaaaga aggccttgct    3540
cttgttaacg aacagcagt tggttctggc ttggcctcta ttgttctatt tgaagctaac    3600
gtgcttgctg tcttatctgt agtgctgtca gcaatctttg ctgccgtgat gactggcaag    3660
cccgagttca ccgatcattt gacgcataag ttgaagcacc atcccggcc              3709
```

<210> SEQ ID NO 45
<211> LENGTH: 62
<212> TYPE: DNA
<213> ORGANISM: Artificial Sequence
<220> FEATURE:
<223> OTHER INFORMATION: Description of Artificial Sequence: pBI101
      Multicloning Region
<220> FEATURE:
<221> NAME/KEY: gene
<222> LOCATION: (58)
<223> OTHER INFORMATION: N at position 58 is a uidA gene
<220> FEATURE:
<221> NAME/KEY: terminator
<222> LOCATION: (62)
<223> OTHER INFORMATION: N at position 62 is a terminator

<400> SEQUENCE: 45

```
aagcttgcat gcctgcaggt cgactctaga ggatccccgg gtggtcagtc ccttatgntg    60 an                                                                    62
```

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: pBI121
      Vector
<220> FEATURE:
<221> NAME/KEY: promoter
<222> LOCATION: (2)
<223> OTHER INFORMATION: N at position 2 is a promoter
<220> FEATURE:
<221> NAME/KEY: gene
<222> LOCATION: (29)
<223> OTHER INFORMATION: N at position 29 is a uidA gene
<220> FEATURE:
<221> NAME/KEY: terminator
<222> LOCATION: (33)
<223> OTHER INFORMATION: N at position 33 is a terminator

<400> SEQUENCE: 46

```
angatccccg ggtggtcagt cccttatgnt gan                                  33
```

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: pBICa2
      Vector
<220> FEATURE:
<221> NAME/KEY: promoter
<222> LOCATION: (2)
<223> OTHER INFORMATION: N at position 2 is a promoter
<220> FEATURE:
<221> NAME/KEY: gene
<222> LOCATION: (29)
<223> OTHER INFORMATION: N at position 29 is a uidA gene
<220> FEATURE:
<221> NAME/KEY: terminator
<222> LOCATION: (33)
<223> OTHER INFORMATION: N at position 33 is a terminator

```
<400> SEQUENCE: 47
angatccccg ggtggtcagt cccttatgnt gan                                    33

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence:  pBIWI
      Vector
<220> FEATURE:
<221> NAME/KEY: promoter
<222> LOCATION: (2)
<223> OTHER INFORMATION: N at position 2 is a promoter
<220> FEATURE:
<221> NAME/KEY: gene
<222> LOCATION: (29)
<223> OTHER INFORMATION: N at position 29 is a uidA gene
<220> FEATURE:
<221> NAME/KEY: terminator
<222> LOCATION: (33)
<223> OTHER INFORMATION: N at position 33 is a terminator

<400> SEQUENCE: 48
angatccccg ggtggtcagt cccttatgnt gan                                    33

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence:  pBalphaTub
      Vector
<220> FEATURE:
<221> NAME/KEY: promoter
<222> LOCATION: (2)
<223> OTHER INFORMATION: N at position 2 is a promoter
<220> FEATURE:
<221> NAME/KEY: gene
<222> LOCATION: (36)
<223> OTHER INFORMATION: N at position 36 is a uidA gene
<220> FEATURE:
<221> NAME/KEY: terminator
<222> LOCATION: (40)
<223> OTHER INFORMATION: N at position 40 is a terminator

<400> SEQUENCE: 49
anatgagagg atccccgggt ggtcagtccc ttatgntgan                             40

<210> SEQ ID NO 50
<211> LENGTH: 271
<212> TYPE: DNA
<213> ORGANISM: Nicotiana tabacum
<220> FEATURE:
<221> NAME/KEY: promoter
<222> LOCATION: (2)
<223> OTHER INFORMATION: N at position 2 is a promoter
<220> FEATURE:
<221> NAME/KEY: gene
<222> LOCATION: (267)
<223> OTHER INFORMATION: N at position 267 is a uidA gene
<220> FEATURE:
<221> NAME/KEY: terminator
<222> LOCATION: (271)
<223> OTHER INFORMATION: N at position 271 is a terminator

<400> SEQUENCE: 50
anatggcatc aaatggtcat gttaatggag gagaaaactt tgagttgtgc aaaaaatcag       60
ctgatccatt gaattgggaa atggcagctg aatccttaag agggagtcat ttggatgaag      120
tgaaaaaaat ggtgagtgaa tttagaaaac caatggtaaa acttggtggt gaaagtttaa      180
```

-continued

```
cagtggcaca agtggctgct agtcatgagc ggaatcgaat tcctgcagcc cggggatccc    240
gatccccggg tggtcagtcc cttatgntga n                                   271
```

```
<210> SEQ ID NO 51
<211> LENGTH: 79
<212> TYPE: PRT
<213> ORGANISM: Nicotiana tabacum

<400> SEQUENCE: 51

Met Ala Ser Asn Gly His Val Asn Gly Gly Glu Asn Phe Glu Leu Cys
  1               5                  10                  15

Lys Lys Ser Ala Asp Pro Leu Asn Trp Glu Met Ala Ala Glu Ser Leu
             20                  25                  30

Arg Gly Ser His Leu Asp Glu Val Lys Lys Met Val Ser Glu Phe Arg
         35                  40                  45

Lys Pro Met Val Lys Leu Gly Gly Glu Ser Leu Thr Val Ala Gln Val
     50                  55                  60

Ala Ala Ser His Glu Arg Asn Arg Ile Pro Ala Ala Arg Gly Ser
 65                  70                  75

<210> SEQ ID NO 52
<211> LENGTH: 13
<212> TYPE: DNA
<213> ORGANISM: Unknown Organism
<220> FEATURE:
<223> OTHER INFORMATION: Description of Unknown Organism: EXEMPLARY
      PROMOTER TATA BOX
<220> FEATURE:
<221> NAME/KEY: unsure
<222> LOCATION: (10)
<223> OTHER INFORMATION: n at position 10 is 1, 2, or 3 a's

<400> SEQUENCE: 52
tcgtatatan cta                                                        13
```

CONSTITUTIVE α-TUBULIN PROMOTER FROM COFFEE PLANTS AND USES THEREOF

The present application is a continuation-in-part of U.S. patent application Ser. No. 09/545,686, filed Apr. 7, 2000, now U.S. Pat. No. 6,441,273, which is hereby incorporated by reference in its entirety. This application claims the benefit of U.S. Provisional Patent Application Ser. No. 60/180,934, filed Feb. 8, 2000, which is hereby incorporated by reference in its entirety.

FIELD OF THE INVENTION

This invention relates to the identification and isolation of DNA promoters from coffee. The invention also relates to a method of protein expression in transgenic plants.

BACKGROUND OF THE INVENTION

Coffee is an agricultural commodity that plays a significant role in the economies of many developing countries. In Colombia, coffee cultivation is restricted to mountain areas with altitudes between 1200 and 1400 meters above sea level. It is especially concentrated in the central region, in an area called the Coffee Zone. With a total annual yield of around 12 million bags, Colombia is ranked second in world production. Of this production, 26% is used for domestic consumption, and the rest is exported to Europe (6 million bags), United States (3 million bags), and Asia (1 million bags), with an average annual market value (1991 to 1995) of $1.6 billion (Banco de la Republica, *Indicadores Economicos NI* 828 Banco de la Republica, Bogota, Colombia (1996)).

The genus *Coffea* belongs to the *Rubiaceae* family which includes other important plants, such as ipecacuanha (*Cephaelis ipecacuanha*) and cinchona (*Cinchona* spp.). The genus contains about 70 species, most of them trees and shrubs growing at low altitudes in the tropical rain forests of Africa and Asia (Sondahl et al., "Coffee," *Biotechnology of Perennial Crops CAB International*, Wallingford, UK (1992)). Only two species are widely cultivated, *Coffea arabica* and *Coffea canephora*. All known species are diploid (2n=2X=22 chromosomes) and obligate outbreeders with self-incompatibility systems, except for *C. arabica* which is tetraploid (2n=4X) and self-fertile.

The species *Coffea arabica* L probably originates from a relatively recent cross between *C. eugenoides* and *C. canephora*, a hypothesis supported by random amplified polymorphic DNA's (RAPD) (Lashermes et al., "Use of Amplified DNA Markers to Analyze Genetic Variability and Relationships of Coffea Species," *Genetic Resources and Crop Evolution* 40:91–99 (1993)) and chloroplast restriction fragment length polymorphism (RFLP) analyses (Lashermes et al., "Inheritance and Restriction Fragment Length Polymorphism of Chloroplast DNA in the Genus *Coffea* L.," *Theoretical and Applied Genetics* 93:626–632 (1996)). The nuclear DNA content of *C. arabica*, as determined by flow cytometry, is 2.4 pg/interphase nucleus, or n=2X=1158 Mb (Arumuganathan et al., "Nuclear DNA Content of Some Important Plant Species," *Plant Molecular Biology Reporter* 9:208–218 (1991)). It is cultivated in 75% of the coffee plantations around the world. The quality of the beverage is potentially excellent, being known in the trade as "mild coffee." The most important pests affecting this species are coffee rust (*Hemileia vastatrix*), coffee berry disease (CBD, *Colletotrichum coffeanum*), and coffee berry borer (*Hypothenemus hampei*, Coleoptera). Worldwide, these three pests cause an estimated crop loss of 14.8%, or about $1 billion annually (Oerke et al., "Estimated Losses in Major Food and Cash Crops," *Crop Production and Crop Protection*, Elsevier, N.Y., U.S.A. (1994)).

Several cultivars have been described for *C. arabica*, but because of the narrow genetic base of the species, they are due mainly to single gene mutations. The commonly grown varieties, Tipica and Bourbon, can grow up to 6 m tall under natural conditions. Coffee trees grow well at tropical elevations, ranging from 300 to 1200 m above sea level, with a mean annual temperature of 18 to 21° C. *C. arabica* cv. Caturra is a mutant of the Bourbon cultivar, which was discovered in Brazil in 1949 and has been extensively grown in Colombia. The main characteristic of this cultivar is the dwarf phenotype resulting from the action of a dominant gene that reduces the internode distance (Orozco, "Descripcion de Especies y Variedades de Café," *CENICAFE* Chinchiná, Caldas (1986)). Use of this phenotype has allowed planting densities to increase from 2500 plants to 10,000 plants/h, which, in turn, has increased bean yields from 5000 kg to about 8000 kg/h.

The species *Coffea canephora* Pierre ex Froehner, also known as *Coffea robusta* Linden, is the diploid species most widely cultivated around the world. It is self sterile and cross pollinated and therefore much more variable than *C. arabica*. *C. canephora* is better adapted to humid-hot climates and is frequently cultivated in low to medium altitudes. The quality of the beverage made from *C. canephora* is usually regarded as inferior to that made of *C. arabica*. However, *C. canephora* is more resistant to coffee rust and CBD.

Traditionally, Tipica, Bourbon, and Caturra were the *C. arabica* cultivars grown in Colombia. These varieties produce a high quality coffee, but they are very susceptible to pests which are not held in balance by natural biocontrol. Although South America was free of the most important coffee pests for many years, threats became real with the appearance of coffee rust in Brazil in 1970 and in Nicaragua in 1976. This disease finally arrived in Colombia in 1983. In anticipation, the Colombian National Center of Coffee Research (CENICAFE), a organization of Colombian coffee growers, began a breeding program for resistance to coffee rust in 1968. The purpose was to create a cultivar of *C. arabica* that preserves the traditional cup quality, but incorporates increased genetic diversity, durable resistance to the coffee rust, phenotypic homogeneity, and productivity (Castillo et al., "La Variedad Colombia: Selección de un Cultivar Compuesto Resistente a la Roya del Cafeto," *CENICAFE Chinchiná, Colombia*, 171 p. (1986)).

Timor hybrid was chosen as the resistant parent of the new cultivar since no germplasm of *C. arabica* was known to contain durable resistance genes against coffee rust. Timor hybrid is a natural interspecific hybrid between *C. arabica* and *C. canephora* found in 1917 on the island of Timor, Indonesia. Used in Africa and India for many years, it showed broad resistance against the local rust races. In the Colombian breeding program, the recurrent quality parent of the new cultivar was *C. arabica* cv. Caturra, which in addition to providing the characteristics of dwarfism and good beverage quality, was a familiar cultivar among the growers. The result was the release in 1980 of the Colombia cultivar, a composite cultivar made up by the mixture of seeds coming from the best F5 and F6 progenies resistant to coffee rust and with optimal adaptation to the climate and soils of the Colombian coffee zone (Castillo et al., "La Variedad Colombia: Selección de un Cultivar Compuesto Resistente a la Roya del Cafeto," *CENICAFE* Chinchiná, Colombia, 171 p. (1986)).

Components of the Colombia cultivar are continuously tested for their resistance against coffee rust and other diseases. When a component is found susceptible, it is withdrawn from the mixture. In the same way, new selected components can be added to the cultivar. This procedure provides a dynamic update of the cultivar in its resistance against coffee rust. Seed production and distribution of the Colombia cultivar are carried out exclusively by the National Federation of Coffee Growers. This maintains a diversity in resistance to coffee rust as well as the phenotypic homogeneity, yet results in low seed prices for the farmers.

In contrast to many other crops, coffee has not been the subject of extensive research in molecular biology. This may be due to factors such as the long life cycle, the difficulty of maintaining plants out of the tropical environment, and the lack of resources from countries that cultivate coffee. Nevertheless, some advances are being made in this field.

Several proteins, especially those involved in the resistant interaction with coffee rust have been studied. Kinetics and differential expression of phenylalanine ammonia lyase (PAL) (Almario, "Study of the Activity of the Phenylalanine Ammonia Lyase in the Presence of the Pathogen in Coffee Varieties Resistant and Susceptible to *Hemileia vastatrix*Ber & Br.," Universidad Nacional de Colombia, Bogota, 155 p. (1992)), superoxide dismutase (Daza et al., "Isoenzyme Pattern of Superoxide Dismutase in Coffee Leaves from Cultivars Susceptible and Resistant to the Rust *Hemileia-Vastatrix*," *Journal of Plant Physiology* 141:521–526 (1993)) and lipoxygenase (Rojas et al., "Stimulation of Lipoxygenase Activity by Cotyledonary Leaves of Coffee Reacting Hypersensitively to the Coffee Leaf Rust," *Physiological and Molecular Plant Pathology* 43:209–219 (1993)) of the Caturra and Colombia cultivars have been compared.

Phenylalanine ammonia lyase (PAL) is a key enzyme that catalyzes the deamination of L-phenylalanine to produce cinnamic acid. Cinnamic acid is a substrate that feeds several biosynthetic routes, leading to the production of various classes of phenylpropanoid-derived secondary plant products. Some of these products are involved in aspects of the normal development of the plant such as petal pigmentation and xylem development. However, many of them are directly involved in the plant defense response (Hahlbrock et al., "Physiology and Molecular Biology of the Phenylpropanoid Metabolism," *Annual Review of Plant Physiology and Plant Molecular Biology* 40:347–369 (1989)).

Activation of PAL can lead to the accumulation of lignin, suberins, and a variety of phenolic esters that increase the strength of cell walls. (Hammond-Kosack et al., "Resistance Gene-Dependent Plant Defense Responses," *The Plant Cell* 8:1773–1791 (1996)). Also, PAL is necessary for the synthesis of flavonoid derivatives that function as pigments, as well as in intracellular signaling, UV protectants, phytoalexins and coumarins, and salicylic acid. PAL is also involved in the synthesis of acetosyrnigone, a wound metabolite that serves as a signal for the activation of virulence (vir)genes in *Agrobacterium tumefaciens*.

PAL is usually encoded by a small gene family of 2 to 6 members. In some plants (e.g., *Solanum tuberosum*), 40 PAL genes can be detected (Joos et al., "Phenylalanine Ammonia Lyase in Potato (*Solanum. tuberosum* L.) Genomic, Complexity, Structural Comparison of Two Selected Clones and Modes Of Expression," *European Journal of Biochemistry* 204:621–629 (1992)), while in loblolly pine (*Pinnus taeda*), there seems to be only one (Whetten et al., "Phenylalanine Ammonia Lyase from Loblolly Pine: Purification of the Enzyme and Isolation of Complementary DNA Clones," *Plant Physiology* 98:380–386 (1992)). It is supposed that different members of the family respond differentially to the induction signals, either in their kinetics of induction, or accumulation of transcripts.

PAL activity is mainly regulated at the level of transcription, by the synthesis of new mRNA (Lois et al., "A Phenylalanine Ammonia-Lyase Gene from Parsley: Structure, Regulation and Identification of Elicitor and Light Responsive Cis-Acting Elements," *EMBO Journal* 8:1641–1648 (1989)). Perturbation of the normal PAL expression in transgenic plants generates abnormal development phenotypes (Elkind et al., "Abnormal Plant Development and Down-Regulation of Phenylpropanoid Biosynthesis in Transgenic Tobacco Containing Heterologous Phenylalanine Ammonia-Lyase Gene," *Proceedings of the National Academy of Sciences of the USA* 87:9057–9061 (1990)). Accumulation of PAL transcripts has been observed in the presence of developmental cues, wounding (Ohl et al., "Functional Properties of a Phenylalanine Ammonia-Lyase Promoter from *Arabidopsis*," *The Plant Cell* 2:837–848 (1990)), hypersensitive response (Dong et al., "Induction of Arabidopsis Defense Genes by Virulent and Avirulent *Pseudomonas Syringae* Strains and by a Cloned Avirulence Gene," *The Plant Cell* 3:61–72 (1991)), ozone fumigation (Sharma et al., "Ozone induced Expression of Stress Related Genes in *Arabidopsis Thaliana*," *Plant Physiology* 105:1089–1096 (1994)), and insect saliva (Hartley et al., "Biochemical Aspects and Significance of the Rapidly Induced Accumulation of Phenolics in Birch Foliage," Tallamy, ed., *Phytochemical Induction in Herbivores*, New York: John Wiley, pp. 105–132 (1991)).

Every cell in the plant has to fulfill basic needs to survive. For this purpose, a set of proteins is constantly present in the cell which is involved in functions such as membrane traffic, membrane stability, cytoplasm organization, transcription apparatus, and primary metabolic pathways. Genes encoding these proteins are called "housekeeping genes," and they are controlled by promoters that are active almost permanently during the cell cycle. Such promoters are called "constitutive." Since the default state of eukaryotic promoters is "off" (contrary to prokaryotic promoters; Lewin, "Genes V.," Oxford University Press, Oxford, UK (1994)), constitutive promoters must contain structural features that enable them to remain active in several tissues and during the multiple developmental stages of the plant. By sequencing, comparing, and modifying plant promoters, it has been possible to identify functional components in their DNA sequence.

In contrast to housekeeping genes, some genes encode products that are only required under special conditions related to developmental stages of the plant, environmental stress, or pathogen attack. These genes contain "inducible promoters" that can be turned on quickly by an inducer agent and are active for a limited length of time before they are turned off again. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent, such as a virus or fungus. A plant cell containing an inducible promoter may be exposed to an inducer by externally applying the inducer to the cell or plant such as by spraying, watering, heating, or by exposure to the operative pathogen. In addition, inducible promoters include promoters that function in a tissue specific manner to regulate the gene of interest within selected tissues of the plant. Examples of such tissue specific promoters include seed, flower, or root specific promoters as are well known in the field (see e.g., U.S. Pat. No. 5,750,385 to Shewmaker et al.). For transgenic plants, these promoters are of interest if accumulation of the protein product, for biological or marketing reasons, is desired in certain tissues, or at certain times.

Genetic engineering provides valuable tools for studying promoter activity. By making constructs in which a reporter gene is fused under the control of a promoter sequence, it is possible to observe the specific activity of the promoter by monitoring the expression of the reporter gene (Herrera-Estrella et al., "Chimeric Genes as Dominant Selectable Markers in Plant Cells," *EMBO Journal* 2:987–995 (1983)). Gene fusion not only provides a way to eliminate variables associated with post-transcriptional regulation from the experiment but also allows comparisons among different promoters or among variations of the same promoter (promoter deletion analysis).

Although a powerful tool in the study of gene control, gene fusion sometimes requires additional analyses in order to provide meaningful results. This is especially true in the characterization of tissue specific promoters. In this case, sequences containing the information for tissue specificity are not only present in the 5' upstream region of the gene, but can also occur in the downstream coding region or even in the 3' end region (Fu et al., "High-Level Tuber Expression and Sucrose Inducibility of a Potato Sus4 Sucrose Synthase Gene Require 5' and 3' Flanking Sequences and the Leader Intron," *Plant Cell* 7:1387–1394 (1995); and Sieburth et al., "Molecular Dissection of the *Agamous* Control Region Shows that Cis Elements for Spatial Regulation are Located Intragenically," *The Plant Cell* 9:355–365 (1997)).

So far, the Colombia cultivar has remained resistant to coffee rust and other coffee pathogens in Colombia. It is possible, nonetheless, that new strains of *Hemileia vastatrix* could be selected for virulence or that new diseases could be introduced to the hemisphere that are pathogenic to the Colombia cultivar. For these reasons, components of the Colombia variety are permanently being screened for resistance against important pathogens, and, taking advantage of the dynamic nature of a multiline, components are continually added to or removed from the final product delivered to the farmers.

Furthermore, there is no known resistance to the coffee berry borer, *Hypothenemus hampei*, at the cultivar or species levels, and, at the time the borer appeared in Colombia (1988), no resistant material had been introduced into the Colombia cultivar. The main obstacle to developing cultivars resistant to coffee berry borer is the lack of resistant parents. Pathogens create a constant selective pressure on the plant population, which has resulted in the co-evolution of the mechanisms of attack and defense (Agrios, "*Plant Pathology*, 4$^{th}$ Ed.," Academic Press, San Diego, U.S.A., 635p (1997)). The natural conditions in which this process develops are altered by the agricultural practice of monoculture which has resulted in enormous crop losses caused by pathogens that have evolved while the host has been held stable.

Because of the low variability present in natural populations of *C. arabica*, resistance must be sought in other species. Even if a related species is found to be resistant, transfer of resistance genes from a wild relative of coffee into the cultivated varieties of *C. arabica* can be difficult or impossible due to interspecific incompatibility and the diploid-tetraploid nature of the cross. Despite that, by use of tissue culture for embryo rescue, crosses between species that are very distant from each other in the phylogenetic tree can be enabled; however, the long term backerossing program needed to select away from characters introgressed from the wild species makes this a difficult option.

SUMMARY OF THE INVENTION

The present invention relates to an isolated DNA promoter suitable for inducing expression of a protein encoded by a second DNA operably associated with the DNA promoter. The DNA promoter of the present invention is isolated from coffee.

The present invention also relates to a DNA construct. The DNA construct has a DNA promoter isolated from coffee, operably linked 5' to a second DNA. The second DNA encodes for a protein or polypeptide, so that transcription of the second DNA is induced. The construct also contains a 3' regulatory region operably linked to the second DNA.

The present invention also relates to transgenic plants and seeds produced by transformation with the DNA construct containing a DNA promoter operably linked to a second DNA encoding a protein or polypeptide.

The present invention also relates to a method of directing protein expression in plants. This involves transforming a plant cell with a DNA construct of the present invention. This construct contains a DNA promoter isolated from coffee that is associated with a second DNA encoding a protein or polypeptide. The DNA promoter induces expression of the second DNA in a plant regenerated from the transformed plant cell.

The present invention also relates to transgenic plants and seeds produced by transformation with the DNA construct containing the DNA promoter isolated from coffee and a DNA encoding a protein.

The present invention also relates to a method of directing protein expression in plants. This involves transforming a plant cell with a DNA construct containing a DNA promoter of the present invention and regenerating a plant from the transformed plant cell. The expression of the second DNA of the DNA construct, under control of the DNA promoter, then occurs in the transformed plant.

The low gene diversity of *Coffea* spp., the lack of resistance to coffee plant pests such the coffee berry borer, and the potential for widespread coffee crop devastation due to pathogen infestation combine to present a serious need for improved methods of coffee plant disease control. In the short term, the options for the farmers are cultural, chemical and biological control. In the long term, the solution is the incorporation of resistance into the Colombia cultivar. With the development of an efficient transformation system, new genes could be introduced into different components of the coffee cultivar, without altering other significant traits of the plants. This option could translate into a reduction of production costs for the farmer, as well as a reduction in pesticide residues on the product and in the environment.

In contrast to sexual breeding, biotechnology can provide a rapid way to transfer genes into coffee in order to improve cultivars that have already been subjected to an extensive selection process for critical factors, such as production, cup quality, and coffee rust resistance.

The present invention provides an important tool for the expression of DNA molecules of choice in plants. This will increase the potential for development of pathogen resistant cultivars of coffee, and improve other characteristics of coffee plants, such as hardiness, production, and cup quality, while overcoming the deficiencies of the methods currently available for fighting disease in the coffee plant.

BRIEF DESCRIPTION OF THE DRAWINGS

FIGS. 1A–D show cloned α tubulin homologous regions in coffee and tobacco. FIG. 1A is a diagram of the general structure of the α tubulin gene in plants from information on these sequences present in the GenBank. In plants, the total number of α tubulin exons has been observed to vary from 3 to 5. For every segment, the minimum and maximum lengths found in the GenBank search are indicated. FIG. 1B shows the consensus sequence (SEQ ID NO: 11) for the 5' end of the cDNA region of the α tubulin gene based on PILEUP alignment from sequences present in the GenBank. The consensus sequence contains part of exon 1, complete exon 2 (bold), and part of exon 3 and was used as a template for primer design. The location of chosen primers is indicated. FIG. 1C and FIG. 1D, respectively, show the nucleotide sequences of the inserts present in pBSTubCof (SEQ ID NO: 41) and pBSTubTob (SEQ ID NO: 42), containing homologous sequences of the α tubulin gene. Primers that allowed the amplification are indicated.

FIGS. 2A–D show cloned PAL exon 1 regions homologous in coffee and tobacco. FIG. 2A is a diagram of the general structure of the PAL gene in plants, from information on these sequences present in the GenBank. For every segment, the minimum and maximum lengths found in the GenBank search are indicated. FIG. 2B shows the consensus sequence (SEQ ID NO: 12) for the 5' cDNA region of the PAL gene based on the PILEUP alignment from the sequences present in the GenBank. The consensus sequence contains part of exons 1 and exon 2 and was used as a template for primer design. The location of chosen primers is indicated by primer name in FIG. 2B. FIGS. 2C and 2D show the nucleic acid sequence of the inserts present in pBSPalTob (SEQ ID NO: 13) and pBSPalCof (SEQ ID NO: 14), respectively, containing homologous sequences of the PAL gene. Primers that allowed amplification are indicated.

FIG. 3 is the nucleic acid sequence of the PAL exan 2 region (SEQ ID NO: 43) amplified in the *Timor* Hybrid.

FIG. 4A shows an agarose gel separation of UP-PCR products, 15 μl per lane. Lane numbers correspond to walking primers as described and numbered in Table 4. FIG. 4B is a Southern Blot of the gel shown in FIG. 4A, probed with pBSTubCof. Positive products are observed with walking primers 6, 7, 11, and 14. The 1.5 kb band in lane 14 was cloned in pBSPrtubCof.

FIGS. 5A–B show the nucleotide sequence and features of the α tubulin promoter from the *Timor* Hybrid, cloned in pBSPrtubCof, which corresponds to SEQ ID NO: 1. Palindromic motifs and direct repeats are indicated by arrows. 23 A-T tetrads (bold) are present in the upstream region of exon 1, and two more are present in intron 1. A potential open reading frame (ORF) with associated TATA and CAAT boxes is present between positions 350 and 573.

FIGS. 6A–C (SEO ID NO. 44) show the nucleic acid sequence and features of the PAL promoter cloned from the *Coffea arabica* genomic library. On the promoter sequence (bases 1–929 of SEQ. ID NO: 44) a putative TATA Box and the elements associated with transcription factors SBF-1 and B-myb are indicated. The subclone also contains the complete sequences of exon 1 and intron 1 and the 5' end of exon 2. The coding region was homologous to the PAL A gene from tobacco.

FIG. 7A is a map of the multicloning region of the pBI101 vector (SEQ ID NO: 45). FIG. 7B is a map of the pBI121vector (SEQ ID NO: 46). The vector contains an 800 bp version of the 35SCaMV promoter inserted between the Hind III and BamHI sites. FIG. 7C is a map of the pBICa2 vector (SEQ ID NO: 47). The double 35SCaMV promoter containing a duplication of the B domain was inserted between the Hind III and BamHI sites. FIG. 7D is a map of the pB1WI vector (SEQ ID NO: 48). The wound inducible ("WI") promoter of the potato proteinase inhibitor gene was inserted between the Hind III and the BamHI sites. FIG. 7E is a map of the pBcctub vector SEO ID NO: 49). A 1041 bp segment upstream of the coffee α tubulin exon 1 and 6 bp of exon 1 from that gene were cloned between the Hind III and the BamHI sites of the multicloning site. The ATG from the α tubulin gene is in-frame with the ATG from the uidA gene.

FIG. 9A shows somatic embryos from *Coffea arabica* cv. Colombia genotype BK620, bombarded with pBI101. A light blue coloration can be observed possibly due to endogenous glucuronidase activity (8×). FIG. 9B shows somatic coffee embryos, bombarded with pBICa2 (8×). FIG. 9C shows somatic coffee embryos, bombarded with pBIαtub (8×). FIG. 9D shows tobacco leaf tissue bombarded with pBIαtub (20×). FIG. 9E shows tobacco cell culture, bombarded with pBIPAL (20×). FIG. 9F shows coffee tissue culture seedlings, bombarded with pBIαtub (8x). FIG. 9G shows coffee tissue culture seedlings, bombarded with pBICa2 (8×).

As shown in FIG. 10A, no activity could be detected in control shoots, or shoots transformed with pBI-PAL (8×). FIG. 10B shows activity at the base of the shoot, observed in transformations with pBI101. This activity is due to the expression of the uidA gene in *Agrobacterium* cells. FIG. 10C shows strong activity observed in shoot transformed with pBICa2 (8×). FIG. 10D shows activity observed in shoots transformed with pBIαtub (8×).

FIG. 11A shows a leaf disk with no expression of GUS (pBI101); 12×. FIG. 11B shows low GUS expression, more evident in the vascular tissue (pBIαtub); 12×. FIG. 11C shows moderate GUS expression (pBIαtub); 12×. FIG. 11D shows high GUS expression, only observed among plants transformed with (pBICa2); 12×. FIG. 11E shows GUS expression in vascular tissue of plants containing pBIPAL; 20×. FIG. 11F shows details of GUS expression on leaf epidermis, vascular tissue, and trichomes (pBIαtub); 20×.

Figure 4A:
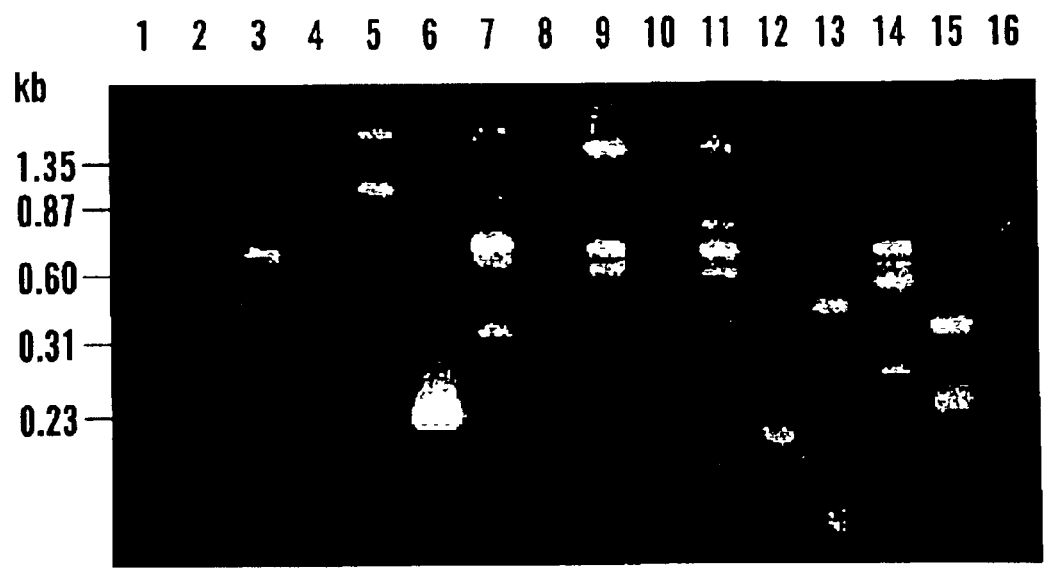
FIGS. 4A–B show the products of the UP-PCR reaction with walking primers ("WP") for the α tubulin gene in *Timor* Hybrid DNA.

Line 1: Non-transformed Tobacco control
Line 2: Transgenic line pBI101-10
Line 3: Transgenic line pBI101-13
Line 4: Transgenic line pBICa2-7 (Medium expresser)
Line 5: Transgenic line pBICa2-20 (Medium expresser)
Line 6: Transgenic line pBICa2-6 (High expresser)
Line 7: Transgenic line pBICa2-9 (High expresser)
Line 8: Transgenic line pBIαtub-7 (Low expresser)
Line 9: Transgenic line pBIαtub-15 (Low expresser)
Line 10: Transgenic line pBIαtub-3 (Medium expresser)
Line 11: Transgenic line pBIαtub-11 (Medium expresser)
Line 12: Transgenic line pBIαtub-5 (High expresser)
Line 13: Transgenic line pBIαtub-12 (High expresser)
Line 14: Transgenic line pBIPAL-15 (Vascular expression)
Line 15: Transgenic line pBIPAL-20 (Vascular expression)
Line 16: Transgenic line pBIPAL-23 (Vascular expression)
Line 17: Non-transformed Tobacco control

DETAILED DESCRIPTION OF THE INVENTION

The present invention relates to an isolated DNA promoter suitable for inducing expression of a protein encoded by a second DNA operably associated with the DNA promoter. The DNA promoter of the present invention is isolated from coffee.

The present invention also relates to a DNA construct. The DNA construct has a DNA promoter isolated from coffee, operably linked 5' to a second DNA encoding a protein or polypeptide to induce transcription of the second DNA. The construct also contains a 3' regulatory region operably linked to the second DNA.

The present invention also relates to transgenic plants and seeds produced by transformation with the DNA construct containing a DNA promoter operably linked to a second DNA encoding a protein or polypeptide.

The present invention also relates to a method of directing protein expression in plants. This involves transforming a plant cell with a DNA construct containing a DNA promoter of the present invention and regenerating a plant from the transformed plant cell. The expression of the second DNA of the DNA construct, under control of the DNA promoter, then occurs in the transformed plant.

The present invention also relates to transgenic plants and seeds produced by transformation with the DNA construct containing the DNA promoter isolated from coffee, and a DNA encoding a protein.

Gene regulation and expression is a complex interaction of intracellular and extracellular factors. It has been estimated that *Arabidopsis thaliana*, with a genome size of 145 Mb, contains about 20,000 genes (National Science Foundation, "The Multinational Coordinated *Arabidopsis Thaliana* Genome Research Project: Year Five," *National Science Foundation*, NSF 96-43 (1995), which is hereby incorporated by reference in its entirety). These genes must be expressed in perfect coordination in order to have organized growth and proper responses to the environment. This is achieved by differential gene expression, in which the plant is able to turn different genes on and off depending on the stage of development, the type of tissue, and specific inducers from the environment.

Plant cells have several mechanisms to control gene expression, and they can be exerted at transcriptional, post-transcriptional, translational and post-translational levels. However, much of the differential expression can be explained at the transcriptional level when the RNA polymerase III interacts with the DNA and multiple protein factors to initiate the synthesis of mRNA (Roeder, "The Role of Initiation Factors in Transcription by RNA Polymerase II," *Trends in Biochemical Science* 21:327–335 (1996), which is hereby incorporated by reference in its entirety). The region of DNA involved in this pre-transcriptional interaction is called the "promoter." Promoters are usually located next to the 5' end of the coding region of a gene.

By sequencing, comparing, and modifying plant promoters, it has been possible to identify functional components in their DNA sequence. All known promoters are made of two general components: the core region and the regulatory region (Kornberg, "RNA Polymerase II Transcription Control," *Trends in Biochemical Science* 21:325–326 (1996), which is hereby incorporated by reference in its entirety).

The core region is located immediately upstream of the 5' end of the coding region and is essential for the transcription process; however, in quantitative terms it is only responsible for a small percentage of the total gene expression. The core region is about 100 bp long and comprises a TATA box and the transcription start site. The TATA box is a sequence of approximately 13 bp, rich in thymidine and adenine residues, with a consensus TC/GTATAT/AA$_{1-3}$C/TA (SEQ ID NO: 52). The TATA box is present in most, but not all, promoters of genes encoding proteins (Roeder, "The Role of Initiation Factors in Transcription by RNA Polymerase II," *Trends in Biochemical Science* 21:327–335 (1996), which is hereby incorporated by reference in its entirety). This is the site of direct interaction with the RNA polymerase II (RNA Pol II) and with universal transcription factors (TAFs), which are a necessary part of the transcription complex (Verrijzer et al., "TAFs Mediated Transcriptional Activation and Promoter Selectivity," *Trends in Biochemical Science* 21:338–342 (1996), which is hereby incorporated by reference in its entirety). General factors are proteins present in all cells and are very conserved from yeast to man (Guarente et al., "Conservation and Evolution of Transcriptional Mechanisms in Eukaryotes," *Trends in Genetics* 8:27–32 (1992), which is hereby incorporated by reference in its entirety).

The regulatory region is located further upstream from the core region and can be as long as 2 kb or even more. This region is responsible for the control of gene expression either suppressing or enhancing the activity of the RNA polymerase II. The regulatory region is composed of several "boxes" or elements that vary in size from 10 to 300 bp. These elements are the binding sites for specific proteins that are involved in the modulation of differential expression of genes and confer cell-specific or gene-specific expression. Proteins at this level interact with TFIID, increasing its stability in promoter binding, therefore enhancing transcription. The presence of multiple elements and their corresponding factors produces a synergistic effect in transcription.

The most dynamic part of the promoter system is the interaction of the protein factors with the DNA and with the other proteins in the complex. For these interactions, proteins must contain structural domains that recognize specific surface characteristics of the minor or major grooves and the sugar-phosphate backbone of the DNA (Travers, "DNA-Protein Interactions," St. Edmundsbury Press, Bury St. Edmunds, Great Britain (1993) which is hereby incorporated by reference in its entirety). The most common domains associated with this function are the helix-turn-helix (HTH) motif, the Zn-binding domain or Zinc fingers, and the Leucine zipper coiled coil (b-ZIP) (Brunelle et al., "Transcription Regulatory Proteins in Higher Plants," *Current Opinions in Genetics and Development* 3:254–258 (1993), which is hereby incorporated by reference in its entirety). Not all transcription regulators bind to DNA. Protein to protein interactions are responsible for the formation of heterodimers or homodimers, which in turn function as positive regulators, or as negative regulators, avoiding formation of active dimers. Synthesis or activation of these factors is induced by particular stimuli and, in some cases, involve phosphorylation cascades (Brunelle et al., "Transcription Regulatory Proteins in Higher Plants," *Current Opinions in Genetics and Development* 3:254–258 (1993), which is hereby incorporated by reference in its entirety).

In the current model for transcription initiation, TBP binds to the TATA box through the minor groove of the DNA helix. TFIIA stabilizes the binding that can be debilitated by altered ionic conditions or mutations in the DNA binding element. TFIIB binds to TBP and orientates its amino terminal domain toward the downstream initiation site. This amino terminal sequence is not conserved among different species which suggests different regulatory pathways (Roeder, "The Role of Initiation Factors in Transcription by RNA polymerase II," *Trends in Biochemical Science* 21:327–335 (1996), which is hereby incorporated by reference in its entirety). Also, plants like Arabidopsis can contain two different TBPs (Gasch et al., "*Arabidopsis Thaliana* Contains Two Genes for TFIID," *Nature* 346:390–394 (1990), which is hereby incorporated by reference in its entirety).

At the same time as TBP binds to the TATA box, TFIIF binds to RNA polymerase II to create a complex that then binds to the amino terminal domain of TFIIB, covering a promoter area of about 40 bp. Finally, TFIIE and TFIIH bind to the complex just upstream of the start site to induce promoter melting (opening of the double strand) and continue with transcription and elongation (Roeder, "The Role of Initiation Factors in Transcription by RNA Polymerase II," *Trends in Biochemical Science* 21:327–335 (1996), which is hereby incorporated by reference in its entirety).

One suitable DNA promoter molecule in accordance with the present invention is a promoter isolated from the coffee plant. One form of the promoter in accordance with the present invention is the α tubulin promoter isolated from *C. arabica* (coffee), which has a nucleic acid sequence corresponding to SEQ ID NO: 1 as follows:

```
aaaagttgta gcgggagggc tggacgatgc gtggagcgga aaatgctgga gtattggacc   60
accaaccaaa caaaatagtt ttagtatatg gggtttcgaa ctttccagtc aacctacaac  120
aatctgcttc tataaacaat aataaaagag taattaaatt actggtagcg ttggtgtatt  180
tggatttgcc agctttgctt ccaaactcat atcatcaatt tgatagcact tggatacgga  240
gatcgctttt gtctgcctta gtatgatatg attgctcacc cgctgtagac atgatttaaa  300
ggaaaataac acaaatatat atatataaga ccaacaaatt ataactgaaa acttttcagt  360
aatgttaatt ctaacacatg tgactagacc tgctatcatc agctgcaatt ctagaggaaa  420
cttggaccag atcagaagtt gtaaagggct gcagtccatt cctgcactat tcagtttgca  480
ggtagatggg tggaccatta tatgatctg gtccagcgtg aatgcagttg tagtaaagac  540
atgttggatt tgttatggat caaactacta ctagtaggga aatgcttcaa agacttctct  600
tgtgattttc tcccagccga atggtccaag tacactagca aaagaagcac aaacggtacc  660
aatgactcga gcgagctgac attttgggct tcagattagc acaagacaaa aggattttc  720 acttttcttc tgtaggtgat cctggactcg caggttggca tgctcaattc aggagctttt  780
gagattggat agggtgttgg ttatgaatgc accgcaggtt gcatgctcaa ttcagagccc  840
ttcacatgta accgtgtgta gcccaggccc aaatgccccg gaagtttaaa ctgaaatctc  900
ggaagagcag atggcaacgg tcgtaattcg tcaagcaatc cgaaacgtcg ccacaccccc  960
acgccagctg gaaaatcagt tcaaaattca aaattcattt tggagccgtt caaacaaaat 1020
tgtttcagtt ttgcccctcg cctgctgccc taatcttacc ccgccattgg ggcttggatt 1080
actcgctcca gtctatatat ataactccct cccgcattgc ctcaccacac gaccccaagt 1140
cctctccttc ttctccttc ccagatctcg gaggtctctc actcttccga tccagagacg 1200
tctttgtata cgcctctggt atctccattc ctcctttttc cctctcttcc aaaaatctcc 1260
tattcatttc tcaaaacatc gcgaaaatga gagagtgcat ctccatccat attggtcagg 1320
ccggtatcca ggtcggaaat gcctgctggg agctctactg cctcgagcac ggcatccagg 1380
```

-continued

```
taaattgcct tctatctaac ctcttatatt tcagatctgc tgtttctctc atttttgttc   1440
aaggaaatga ttcatctttg gtttgatttt gggtgttgtg gaatagcctg atggacaaat   1500
gccgagcgac cacaccgtcg gaggcggaga cgacgctttc aacaccttct tcagcgaaac   1560
cggagccggc aaacacgttc ctcgtgccgt gttcgtcgat ctggagccca ctgtcatcga   1620
tgaagtccga accggcacct accgccaact cttccaccct gagcagctca t             1671
```

A second DNA promoter in accordance with the present invention is also found in C. arabica. This is the phenylalanine ammonia lyase (PAL) promoter which has a nucleic acid sequence corresponding to SEQ ID NO: 2 as follows:

have the DNA expressed under control of a DNA promoter isolated from coffee.

Examples of other DNA molecules that could be expressed in the present invention include, but are not

```
catttcttgc cagaaagcac tagtgaatat tctatccctg tcagtcacta tagattctgg    60
aagtccatgt aatctaaaaa tgtttccagg aagagttgag ccacctgttt ggttgtgaag   120
gggtgagcta aggcaagcaa atgacctact ttggacaacc tatcaatcac caccatcact   180
gtattatatc cttgagattc tggaaggctc tctatgaagt ccatggttag gtgagtccaa   240
gctaaacgag gaataggtga tggttgtagc agtccaaggt agggtccatg ctttgactta   300
aatctttggc atatgtcaca agcatgaata tacctgatga ttttccccaa atgttttga    360 ggttttaat accgggaatg gcccaggaaa aagggccctg gctttgcacc aaggtcccct    420
aagaatttct ggcaaaagtt caagcggttc caaagtgccc caatgggacc tctccaaaaa   480
aggtgccccg gggacaagtt gtgctcagtt cggcgcgttt caagacaggt tttggccaga   540
aagcaaaggg gttccaaagg gtgtcagagg gtccatgttt caaaactccg ggtgtcttgg   600
tcccccataa ttgacttcgg ctaagtaaag gaaaaccttga gccgaggctg taattaagcc   660
gaagtcctaa cgcgatggcg aacggccgag gtggtcggag cctaagagac ataggcggga   720
ccccagctct gccgacctgg aaatacccctc ctcatatacc attactagtt agtagtcacc   780
actgctactg cttcagttcc ttttatcact tgctttacat gaattaagtc gatgctcttc   840
cttgaataac tagcgattag tttcgtggtg acctatctag ccattttct gtttgggtgg    900 catcaatcct gaacacagaa agctgcaag                                      929
```

These promoters can be used in a DNA construct with a protein-encoding DNA which produces a wide variety of proteins. Protein-encoding DNA suitable for use in the present invention include DNA which has been amplified, chemically altered, or otherwise modified. Modification of such protein-encoding DNAs may occur, for example, by treating the DNA with a restriction enzyme to generate a DNA fragment which is capable of being operably linked to the promoter. Modification can also occur by techniques such as site-directed mutagenesis.

The protein-encoding DNA also includes DNA that is completely synthetic, semi-synthetic, or biologically derived, such as DNA derived by reverse transcription from RNA. Such DNA includes, but is not limited to, non-plant genes such as those from bacteria, yeasts, animals, or viruses; modified genes, portions of genes, chimeric genes, as well as DNA that encodes for amino acids that are chemical precursors or biologics of commercial value, such as polymers or biopolymers. (Pool et al., "In Search of the Plastic Potato," Science 245:1187–1189 (1989), which is hereby incorporated by reference in its entirety.) Suitable DNA is any DNA for which expression is beneficial to the transgenic plant or for which it is otherwise beneficial to limited to, hypersensitive response elicitor genes derived from bacterium, such as those encoding the harpin protein isolated from Erwinia amylovora and Erwinia chrysanthemi (U.S. Pat. No. 5,849,868 to Beer et al., which is hereby incorporated by reference in its entirety), the hrpZ gene isolated from Pseudomonas syringae pv syringae (U.S. Pat. No. 5,858,768 to Collmer et al., which is hereby incorporated by reference in its entirety), and viral replicase genes derived from plant pathogens, which confer pathogen resistance to transformed plants (U.S. Pat. Nos. 5,633,449 and 5,945,581 to Zaitlin et al., which are hereby incorporated by reference).

The DNA construct of the present invention also includes an operable 3' regulatory region, selected from among those which are capable of providing correct transcription termination and polyadenylation of mRNA for expression in plant cells, operably linked to the a DNA molecule which encodes for a protein of choice. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," Proc. Nat'l Acad. Sci. USA, 80:4803–4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature,* 313(6005):810–812 (1985), which is hereby incorporated by reference in its entirety). Virtually any 3' regulatory region known to be operable in plants would suffice for proper expression of the coding sequence of the DNA construct of the present invention.

The DNA molecule, the promoter of the present invention, and a 3' regulatory region can be ligated together using well known molecular cloning techniques as described in Sambrook et al., *Molecular Cloning: A Laboratory Manual,* Second Edition, Cold Spring Harbor Press, NY (1989), which is hereby incorporated by reference in its entirety.

The DNA construct can also include a DNA molecule encoding a secretion signal. A number of suitable secretion signals are known in the art and others are continually being identified. The secretion signal can be a DNA leader which directs secretion of the subsequently translated protein or polypeptide, or the secretion signal can be an amino terminal peptide sequence that is recognized by a host plant secretory pathway. The secretion-signal encoding DNA molecule can be ligated between the promoter and the protein-encoding DNA molecule, using known molecular cloning techniques as described in Sambrook et al., *Molecular Cloning: A Laboratory Manual,* Second Edition, Cold Spring Harbor Press, New York (1989), which is hereby incorporated by reference in its entirety.

A further aspect of the present invention relates to an expression system that includes a suitable vector containing a DNA construct of the present invention. In preparing the DNA construct for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens,* a soilborne bacterium that causes crown gall. Crown gall is characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTI, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *A. tumefaciens.* (Fraley, et al., "Expression of Bacterial Genes in Plant Cells," *Proc. Nat'l Acad. Sci.,* 80: 4803–4807 (1983), which is hereby incorporated by reference in its entirety.)

Further improvement of this technique led to the development of the binary vector system. Bevan, M., "Binary *Agrobacterium* vectors for plant transformation," *Nucleic Acids Res.* 12:8711–8721 (1984), which is hereby incorporated by reference in its entirety. In this system, all the T-DNA sequences (including the borders) are removed from the pTi, and a second vector containing T-DNA is introduced into *A. tumefaciens.* This second vector has the advantage of being replicable in *E. coli* as well as *A. tumefaciens,* and contains a multiclonal site that facilitates the cloning of a transgene. An example of a commonly used vector is pBin19. Friscb, et al., "Complete Sequence of the Binary Vector Bin19," *Plant Molec. Biol.* 27:405–409 (1995), which is hereby incorporated by reference in its entirety. Any appropriate vectors now known or later described for plant transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures, including prokaryotic organisms and eukaryotic cells grown in tissue culture. A further aspect of the present invention includes a host cell which includes a DNA construct of the present invention. As described more fully hereinafter, the recombinant host cell can be either a bacterial cell (e.g., *Agrobacterium*) or a plant cell. In the case of recombinant plant cells, it is preferable that the DNA construct is stably inserted into the genome of the recombinant plant cell.

The DNA construct can be incorporated into cells using conventional recombinant DNA technology. Generally, this involves inserting the DNA construct into an expression vector or system to which it is heterologous (i.e., not normally present). As described above, the DNA construct contains the necessary elements for the transcription and translation in plant cells of the heterologous DNA molecule.

Once the DNA construct of the present invention has been prepared, it is ready to be incorporated into a host cell. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual,* Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell.

Accordingly, another aspect of the present invention relates to a method of making a recombinant plant cell. Basically, this method is carried out by transforming a plant cell with a DNA construct of the present invention under conditions effective to yield transcription of the DNA molecule in response to the promoter. Methods of transformation may result in transient or stable expression of the DNA under control of the promoter. Preferably, the DNA construct of the present invention is stably inserted into the genome of the recombinant plant cell as a result of the transformation, although transient expression can serve an important purpose, particularly when the plant under investigation is slow-growing.

The gene fusion system that generates chimeric molecules is a very powerful tool to study promoter activity. However, although many transformation and regeneration protocols have been developed for plants, it still takes at least 3 months (in the case of tobacco) or as long as 1 year (as in coffee) to obtain stable transformant plants that can be evaluated. Even then, more time is required to evaluate expression in tissues like flowers or fruits. As an alternative methodology, transient expression in tissue or protoplasts offers a fast and often reliable way to generate information before proceeding with stable transformation. In addition, this method circumvents possible negative "position effects" due to the insertion of the introduced DNA into non-expressing regions of the chromosome.

Transient expression in plant tissue is often achieved by particle bombardment (Klein et al., "High-Velocity Microprojectiles for Delivering Nucleic Acids Into Living Cells," *Nature* 327:70–73 (1987), which is hereby incorporated by reference in its entirety). In this method, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used. Transient gene expression after particle bombardment of leaves and cell cultures of coffee has been used to test different constructs containing the uidA gene (Van et al., "Transient Expression of Beta-Glucuronidase Following Biolistic Delivery of Foreign DNA Into Coffee Tissues," *Plant Cell Reports* 14:748–752 (1995), which is hereby incorporated by reference in its entirety).

Transient expression in protoplasts allows quantitative studies of gene expression since the population of cells is very high (on the order of $10^6$). To deliver DNA inside protoplasts, several methodologies have been proposed, but the most common are electroporation (Fromm et al., "Expression of Genes Transferred Into Monocot and Dicot Plants by Electroporation," *Proceedings of the National Academy of Science USA* 82:5824–5828 (1985), which is hereby incorporated by reference in its entirety) and polyethylene glycol (PEG) mediated DNA uptake (Krens et al., "In Vitro Transformation of Plant Protoplasts with Ti-Plasmid DNA," *Nature* 296:72–74 (1982), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high.

Although a very useful technique, transient expression falls short when the tissue to be examined is difficult to bombard (meristems or floral tissue) or the isolation of protoplasts is troublesome. In addition, transient expression is not feasible in some cases of gene induction, such as by wounding or by certain pathogens, or when spatial or temporal patterns of expression of a gene are under study. For these reasons, generation of stable transgenic plants may still be required.

Another method of introducing the DNA construct into plant cells is to infect a plant cell with *Agrobacterium tumefaciens* or *Agrobacterium rhizogenes* previously transformed with the DNA construct. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

Stable expression of foreign genes in plants has been achieved systematically since 1983 by using *Agrobacterium* mediated DNA transfer (Fraley et al., "Expression of Bacterial Genes in Plant Cells," *Proceedings of the National Academy of Sciences of the U.S.A.* 80:4803–4807 (1983), which is hereby incorporated by reference in its entirety). As described in detail above, genetic manipulation of *Agrobacterium* makes it useful as a tool with which to transfer foreign DNA into a plant.

Infection of *C. arabica* and *C. canephora* with *Agrobacterium tumefaciens* and *Agrobacterium rhizogenes*, as well as production of transgenic calli and plantlets expressing the neomycin phosphotransferase gene (npt II) and the *E. coli* β-glucuronidase gene (uidA), have been reported. Spiral et al., "Regeneration of Plantlets of *Coffea canephora* Pierre Robusta Transformed by *Agrobacterium rhizogenes*," *Comptes Rendus de Academic des Sciences Serie III Sciences de la vie* 316:1–6 (1993); Freire et al., "Genetic Transformation of Coffee (*Coffea arabica* L.)," 91$^{st}$ Annual Meeting of the American Society for Horticultural Science, Corvallis, Oreg., USA, August 7–10, *Hortscience* 29:454 (1994); and Sugiyama et al., "Transformation of Coffee with *Agrobacterium rhizogenes*," Association Scientific Internationale du Café, 16th International Scientific Colloquium on Coffee, Vols. 1 and 2; Kyoto, Japan, Apr. 9–14, 1995 500 p.(vol. 1) (1995), which are hereby incorporated by reference. However, no further genetic characterization of any of those regenerants has been reported so far.

Since not all the plants, and especially monocotyledonous species, can be transformed by *Agrobacterium*, alternative transformation procedures such as particle bombardment and PEG transformation of protoplasts, described above, have also been used successfully to generate stable transformants.

Plant tissue suitable for transformation include, but are not limited to leaf tissue, root tissue, meristems, zygotic and somatic embryos, megaspores and anthers.

After transformation, the transformed plant cells can be selected and regenerated. Preferably, transformed cells are first identified using a selection marker simultaneously introduced into the host cells along with the DNA construct of the present invention. The most widely used reporter gene for gene fusion experiments has been uidA, a gene from *Escherichia coli* that encodes the β-glucuronidase protein, also known as GUS. (Jefferson et al., "GUS Fusions: β Glucuronidase as a Sensitive and Versatile Gene Fusion Marker in Higher Plants," *EMBO Journal* 6:3901–3907 (1987) which is hereby incorporated by reference in its entirety). GUS is a 68.2 kd protein that acts as a tetramer in its native form. It does not require cofactors or special ionic conditions, although it can be inhibited by divalent cations like $Cu^{2+}$ or $Zn^{2+}$. GUS is active in the presence of thiol reducing agents like β-mercaptoethanol or dithiothreitol (DTT).

In order to evaluate GUS activity, several substrates are available. The most commonly used are 5 bromo-4 chloro-3 indolyl glucuronide (X-Gluc) and 4 methyl-umbelliferyl-glucuronide (MUG). The reaction with X-Gluc generates a blue color that is useful in histochemical detection of the gene activity. For quantification purposes, MUG is preferred, because the umbelliferyl radical emits fluorescence under UV stimulation, thus providing better sensitivity and easy measurement by fluorometry (Jefferson et al., "GUS Fusions: β Glucuronidase as a Sensitive and Versatile Gene Fusion Marker in Higher Plants," *EMBO Journal* 6:3901–3907 (1987) which is hereby incorporated by reference in its entirety). Other suitable selection markers include, without limitation, markers encoding for antibiotic resistance, such as the nptII gene which confers kanamycin resistance (Fraley, et al., *Proc. Natl. Acad. Sci. USA*, 80:4803–4807 (1983), which is hereby incorporated by reference in its entirety) and the dhfr gene, which confers resistance to methotrexate (Bourouis et al., *EMBO J.* 2:1099–1104 (1983), which is hereby incorporated by reference in its entirety). A number of antibiotic-resistance markers are known in the art and others are continually being identified. Any known antibiotic-resistance marker can be used to transform and select transformed host cells in accordance with the present invention. Cells or tissues are grown on a selection medium containing an antibiotic, whereby generally only those transformants expressing the antibiotic resistance marker continue to grow. Similarly, enzymes providing for production of a compound identifiable by luminescence, such as luciferase, are useful.

Also suitable as selection markers for the present invention are genes that cause the overproduction of a plant product, such as the cytokinin-synthesizing ipt gene from *A. tumefaciens*. Localized over-production of the plant hormone, cytokinin, can be determined by known methods, such as ELISA assay. Hewelt et al., "Promoter Tagging with a Promoterless ipt Gene Leads to Cytokine-induced Phenotypic Variability in Transgenic Tobacco Plants: Implications of Gene Dosage Effects," *Plant J.* 6:879–91 (1994), which is hereby incorporated by reference in its entirety. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom.

Tissue culture of coffee was developed initially as a supplemental technique to traditional breeding. Somaclonal variation was initially used to generate genetic variation in vitro in order to obtain plants with increased disease resistance or with reduced caffeine levels. Presently, coffee tissue culture techniques are used to study secondary metabolites, to produce homozygous lines, to recover interspecific embryos, and in the production of transgenic lines (Sondahl et al., "Coffee," *Biotechnology of Perennial Crops CAB International*, Wallingford, UK (1992), which is hereby incorporated by reference in its entirety).

The most common tissue culture method for coffee regeneration is through somatic embryogenesis. Since 1970, several reports have indicated the ability of coffee leaves and orthotropic shoots to generate somatic embryos at high or low frequencies (Sondhal et al., "High Frequency Induction of Somatic Embryos in Cultured Leaf Explants of *Coffea arabica*," *L.Z. Pflanzenphysiol.* 81:395–408 (1977), which is hereby incorporated by reference in its entirety). In the high frequency somatic embryogenesis pathway (HFSE) the tissue goes through a callus stage before giving rise to embryos. In contrast, the low frequency somatic embryogenesis (LFSE) does not require callus formation and produces embryos directly from explants. More recently, regeneration has been obtained from protoplasts isolated from embryogenic cell suspension cultures (Acuña et al., "Plant Regeneration from Coffee Protoplasts of Embryonic Cell Suspensions of *Coffea arabica* L. cv. Caturra," *Plant Cell Reports* 10:345–348 (1991), which is hereby incorporated by reference in its entirety). Methodologies that make use of somaclonal variation and protoplast transformation have already been patented (U.S. Pat. No. 5,436,395 to Sondahl et al., and U.S. Pat. No. 5,334,529 to Adams et al., which are hereby incorporated by reference).

Other methods of plant regeneration known to those skilled in the art may be used in the present invention such as those described in Evans, et al., *Handbook of Plant Cell Cultures, Vol. 1*: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference.

It is known that practically all plants can be regenerated from cultured cells or tissues, including but not limited to, all major species of coffee, alfalfa, rice, wheat, barley, rye, cotton, sunflower, peanut, corn, potato, sweet potato, bean pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the DNA construct is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field.

Once transgenic plants of this type are produced, the plants themselves can be cultivated in accordance with conventional procedures. Alternatively, transgenic seeds are recovered from the transgenic plants. The seeds can then be planted in the soil and cultivated using conventional procedures to produce transgenic plants.

Recovery of the product of expression of any heterologous DNA of choice used in the present invention will depend on the exact nature of the product, and the technique chosen for recovery will be known to those skilled in the art.

Although location in the genome and presence of specific sequences are good indicators for identifying promoter sequences, the final test is the ability to control the expression of a transgene in plant transformation experiments.

EXAMPLES

Example 1

Genoinic Miniprep DNA Extraction

For DNA minipreparations (Cheung et al., "A Simple and Rapid DNA Microextraction Method for Plant, Animal and Insect Suitable for RAPD and Other PCR Analyses," *PCR Methods and Applications* 3:69–70 (1993), which is hereby incorporated by reference in its entirety) coffee and tobacco seeds were germinated in soil, and approximately 25 mg of leaf tissue was immersed in 160 μl of extraction buffer (200 mM Tris-HCl pH 8.0, 70 mM EDTA, 2M NaCl, 20 mM sodium metabisulfate, 2% hexadecyltrimethyl ammonium bromide (CTAB), and 0.2% β-mercaptoethanol). The tissue was ground with an electric-driven Kontes pestle for about 30 seconds and 40 μl of 5% Sarkosyl was added. The lysate was incubated for 1 hour at 60° C. and centrifuged at room temperature for 15 minutes at 16,000 g to remove cell debris. The supernatant was transferred to a clean tube, and DNA was precipitated by the addition of 90 μl of 10 mM ammonium acetate and 200 μl of isopropanol, incubated at room temperature for 15 minutes. Total DNA was pelleted by centrifuging at 16,000 g for 15 minutes at 4° C., and rinsed with 70% ethanol. After drying for 1 minute under vacuum, the DNA was resuspended in 50 μl of type 1 water.

Example 2

Genomic DNA Maxiprep Extraction

For DNA maxipreparations, the protocol from Bernatzky et al., "Toward a Saturated Linkage Map in tomato Based on Isozymes and Random cDNA Sequences," *Genetics* 112: 887–898 (1986), which is hereby incorporated by reference in its entirety, was slightly modified as follows: coffee or tobacco leaves from greenhouse plants (7–10 g) were collected, washed with tap water, and after that, immersed and blended for 1–2 minutes in 150 ml of DNA extraction buffer (63.77 g sorbitol, 12.1 g Trizma base, 1.86 EDTA-Na$_2$, 0.2% β-mercaptoethanol, pH 8.2, made up to 1 liter with water; 0.19 g sodium bisulfite was added just before use). The resulting mixture was filtered through a layer of miracloth and two layers of cheesecloth into 250 ml plastic bottles kept on ice. After centrifugation at 4° C. for 15 minutes at 650 g, the supernatant was discarded and the pellet resuspended in 5 ml of DNA extraction buffer to be transferred to a 50 ml Falcon tube containing 2 ml of 5% Sarkosyl. The bottle was rinsed with 5 ml of nuclei lysis buffer (0.2 M Tris, 50 mM EDTA, 2 M NaCl, 20 g CTAB, pH 7.5) and added to the 50 ml tube, which was then incubated at 65° C. for 15–60 minutes. The mixture was extracted once with 15 ml of a chloroform:octanol mixture (24:1) by inverting the tube until an emulsion was obtained. The tube was centrifuged for 15 minutes at 480 g and the aqueous phase was transferred to a new 50 ml tube using wide bore tips. An equal volume of chilled isopropanol was added, and the tube was inverted gently until DNA formed a precipitate that was then hooked out using a bent Pasteur pipette. DNA was rinsed in 70% ethanol and excess ethanol was removed on a Kimwipe tissue. DNA was transferred to a new microfuge tube and resuspended in 100 μl of water by incubation in a 65° C. water bath for 30–60 minutes. Starch was removed by centrifugation at 16,000 g for 10 minutes at room temperature. Final DNA concentration was determined by absorption at 260 nm (dsDNA concentration μg/ml= A$_{260}$×dilution factor×50), and DNA quality water was checked by running in a 1% agarose gel a mixture of 10 ml of water, 5 ml of the maxipreparation DNA and 5 ml of gel loading buffer.

Example 3

Genomic DNA Restriction Digestion

For genomic DNA restriction digestion, 10–15 μg of genomic DNA was incubated with 100 U of the restriction enzyme and 5 μl of buffer, in a final reaction volume of 50 μl, at 37° C., overnight. The reaction was loaded in a 0.8% agarose gel and run at 25 volts for several hours.

Example 4

Nonradioactive Labeling of Probes by PCR

Cloned inserts form pBluescript were excised with EcoRI and Hind III and separated in 1.5% agarose gel. Appropriate bands were cut from the gel under illumination with UV 33 nm, and DNA was purified from the gel using the Prep-A-Gene Kit (BioRad). For labeling with digoxigenin (DIG) (Lanzillo, "Preparation of Digoxigenin-Labeled Probes by the Polymerase Chain Reaction," *Biotechniques* 8:621–622 (1990), which is hereby incorporated by reference in its entirety), DNA fragments were used as a template in a standard 100 μl PCR reaction containing 10 pmoles each of dATP, dGTP, and dCTP, and 6.5 pmoles of dTTP, and 3.5 pmoles of digoxigenin-11-dUTP. The yield of DIG-labeled DNA was estimated by colorimetric detection with nitroblue tetrazolium (NBT) and 5-bromo-4-chloro-3-indolyl phosphate (X-phosphate), according to manufacturer's directions for the GENIUS III Kit (Boehringer Mannheim, Indianapolis, Ind.).

Example 5

DNA Dot and Southern Blots

DNA dot blots were done by incubating 9 μl of PCR product with 1 μl of denaturing solution (4M NaOH, 100 mM EDTA) at room temperature for 10 minutes. 1 μl of this solution was later spotted twice on a piece of nylon membrane (Genescreen Plus, NEN Research Products,) and dried on the bench at room temperature.

For Southern blots, DNA (plasmid or genomic) was initially separated in an agarose gel, then denatured by immersing the gel in denaturing solution (0.5 N NaOH, 1.5 M NaCl) for 30 minutes, neutralized in neutralization solution (1.0 M Tris-HCl pH 8.0, 1.5 M NaCl) for 30 minutes and finally blotted overnight by capillary transfer to the nylon membrane (Geneplus, NEN) using 10×SSC buffer (1.5 M NaCl, 150 mM sodium citrate, pH 7.0).

Hybridization was done after washing the membrane with 5×SCC containing 0.1% sodium dodecyl sulfate (SDS) for 5 minutes at room temperature, loading it in hybridization tubes and then blocking the membrane for 2 hours in a rotating oven at 60–65° C. with standard prehybridization solution (5×SCC, 1.0% (w/v) blocking reagent, 0.1% N laurylsarcosine, 0.02% SDS). Finally, DIG-labeled probe was dissolved in standard prehybridization solution to a final concentration of 20 ng/ml, boiled for 10 minutes, cooled down to 60–65° C. and added to the hybridization tube for overnight incubation. Membrane development was done according to the manufacturer's protocol for chemiluminescent detection using Lumigen (GENIUS III Kit, Boehringer Mannheim). Film was then placed on top of the membrane, and exposed for 5–30 minutes before developing.

Example 6

Identification of Consensus Sequences

Exploration of DNA information present in the GenBank was performed in order to study and clone orthologous sequences present in the coffee genom. As shown in Table 1, a comparison of regions from genes expressed constitutively, and involved in plant defense, found that in the coding regions the similarity was high, but in promoter and intron regions similarity was low. Promoters of interest generally can be pursued by the traditional method of screening genomic libraries, or it can be assisted by the use of standard PCR techniques. The lack of significant homology among promoter regions requires the use of modified techniques in order to amplify those sequences in plants like coffee. Since both screening of genomic libraries or PCR techniques require the use of one flanking region, the one that can that can be used for promoter cloning in coffee is any of the conserved exons located downstream of the promoter. From the results of the homology study, as indicated in Table 1, it was predicted that coding regions in coffee could be obtained using primers that align to very conserved sequences, and that novel promoters and introns could be isolated.

lowest annealing temperature after the first 15 cycles. Then, annealing temperatures went up again every 5 cycles until the original high temperature was reached. The amplification of conserved regions was favored by the use of a modified "touchdown" PCR technique, in which the use of low annealing temperatures allows the 3' ends of the primers to align to highly similar sequences present in the coffee and tobacco templates, but tolerating mismatches in the center and 5' end regions of the primers. Touchdown PCR avoids the need to run several PCR reactions at different annealing temperatures, which is usually done to standardize primer-pair conditions in a specific template. Using this technique, it was possible to run the same PCR profile for 8 different primer pairs on two templates (tobacco and coffee DNA) and amplify the specific products without accumulation of

TABLE 1

| Gene | Sequences | Promoters | Genera | cDNA | 1 kb Downstream | 1 kb Upstream |
|---|---|---|---|---|---|---|
| β tubulin | 67 | 12 (18%) | 6 | 70.8 ± 4.1 | 47.7 ± 6.6 | 25.7 ± 2.0 |
| α tubulin | 54 | 5 (9%) | 2 | 73.8 ± 6.9 | 30.3 ± 3.6 | 23.5 ± 2.6 |
| Actin | 125 | 9 (7%) | 2 | 55.5 ± 18.6 | 40.3 ± 19.2 | 23.0 ± 1.3 |
| CHS | 152 | 37 (24%) | 12 | 64.2 ± 10.5 | 36.9 ± 14.3 | 23.6 ± 1.9 |
| PAL | 71 | 21 (29%) | 10 | 63.4 ± 7.5 | 39.3 ± 15.2 | 25.8 ± 8.7 |
| ACC | 54 | 10 (18%) | 7 | 49.3 ± 10.4 | 40.1 ± 10.3 | 23.6 ± 2.6 |
| SOD | 74 | 9 (12%) | 5 | 52.2 ± 12.6 | 32.3 ± 10.0 | 23.9 ± 2.6 |
| LOX | 83 | 13 (15%) | 6 | 44.1 ± 11.1 | 29.0 ± 4.8 | 24.4 ± 2.9 |
| Total | 680 | 116 (17%) | 22 | | | |

CHS = chalcone synthase
PAL = phenylalanine ammonia lyase
ACC = amino cyclopropane 1 carboxylate synthase
SOD = Cu/Zn superoxide dismutase
LOX = lipoxygenase Consensus sequences were obtained by multiple alignments of the GenBank sequences, using the PILEUP program from the GCG Software package (Deveraux et al., "A Comprehensive Set of Sequence Analysis Programs for the VAX," Nucleic Acids Research 12:387–395 (1984), which is hereby incorporated by reference in its entirety). Primers aligning to very conserved DNA regions were designed using the consensus sequences as templates in the computer program PRIMER 0.5 (Lincoln et al, "PRIMER": A Computer Program for Automatically Selecting PCR Primers. Version 0.5 software, Whitehead Institute for Biomedical Research, Cambridge, Mass. (1991), which is hereby incorporated by reference in its entirety), and these primers were used to amplify the corresponding homologous regions from genomic leaf DNA from tobacco and coffee by standard PCR. Standard PCR reactions were done in volumes of 100 μl containing 100–200 ng of either *Nicotiana tabacum* var. Havana or *Coffea* var. Timor Hybrid DNA, or 10–20 ng plasmid DNA, in addition to 150 ng of each primer at 25 pmoles, 200 μM of each deoxynucleotide, 2.0 mM Mg C12 and 10 μl 10× Taq buffer. The reaction was then covered with 100 μl of mineral oil and placed in an Omnigene Thermocycler (Hybaid, Middlesex, UK). An initial "Hot Start" was performed by doing a denaturation step of 95° C. for 5 minutes before adding 5 μl of a solution containing 2.5 U Taq polymerase (Promega, Madison, Wis.), and continuing with the desired profile. The original "touchdown PCR" profile (Don et al., "'Touchdown' PCR to Circumvent Spurious Priming During Gene Amplification," Nucleic Acids Research 19:4008(1991), which is hereby incorporated by reference in its entirety) was modified as follows: annealing temperatures were changed every 5 cycles along the profile, starting with a high annealing temperature and reaching the undesired alternative products. A modified "Touchdown" PCR profile, as shown in Table 2, was used to amplify the conserved region of α tubulin and PAL genes in coffee and tobacco.

TABLE 2

95° C. × 5 minutes
Addition of Taq polymerase

94° C. × 30 sec/55° C. × 30 sec/72° C. × 15 sec/5 cycles
94° C. × 30 sec/50° C. × 30 sec/72° C. × 15 sec/5 cycles
94° C. × 30 sec/45° C. × 30 sec/72° C. × 15 sec/5 cycles
94° C. × 30 sec/50° C. × 30 sec/72° C. × 15 sec/5 cycles
94° C. × 30 sec/55° C. × 30 sec/72° C. × 15 sec/5 cycles
72° C. × 3 minutes Table 3 shows the Sequence of the primers obtained for α tubulin (exons 1 and 2) and PAL genes (exon 1) after comparing the results from the PRIMER program and the consensus region. The 3' end of these primers lies on very conserved regions.

TABLE 3

```
                                       SEQ ID NO:3
ALP-F40ggaattcggt atccaggtcg gaaac SEQ ID NO:4
ALP-F59ggaattcgtg ctgggagctc tactg SEQ ID NO:5
ALP-R247gcaagcttac agtgggttca agatcaac
```

TABLE 3-continued

```
                            SEQ ID NO:6
ALP-R304gcaagcttat gagctgctca gggtgg SEQ ID NO:7
PAL-F25ggaattcgct gctgagtcaa tgaaagg SEQ ID NO:8
PAL-F39ggaattcgaa agggagtcat ttggatg SEQ ID NO:9
PAL-R127gcaagcttat actatccatc acccaatcac SEQ ID NO:10
PAL-R133gcaagcttgt tcatactatc catcaccc
```

Example 7

Cloning of PCR Fragments Based on Consensus Sequences

PCR fragments were cloned by blunt-ending the PCR products with 2 U of T4 DNA polymerase (New England Biolabs, Beverly, Mass.) added directly to a 100 µl PCR reaction and incubated at 25° C. for 20 minutes, followed by 70° C. for 15 minutes to inactivate the polymerase. The total volume of the PCR reaction was then rinsed and concentrated using an Ultrafree-MC filter unit 30,000 NMWL low-binding PLTK membrane (Millipore, Bedford, Mass. adding 300 µl of water and centrifuging at 8,000 g for 5 minutes, three times obtaining a final volume of approximately 25 µl. Afterwards, approximately 400–700 ng of blunt-ended PCR product was added to a 15 µl ligation reaction containing 400 ng of pBluescript SK- (Stratagene, LaJolla, Calif.), following digestion with EcoRV.

Competent *E. coli* DH5 α cells were transformed and grown overnight on LB plates according to standard procedures (Sambrook et al., "Molecular Cloning: A Laboratory Manual," Cold Spring Harbor, N.Y.: Cold Spring Harbor Press (1989), which is hereby incorporated by reference in its entirety). Positive clones were selected, subjected to a round of PCR to identify recombinants, and after agarose gel resolution of the PCR products, colonies containing recombinant plasmids of the expected size were selected for either sequencing or dot blot tests with digoxin-labeled probes.

Example 8

DNA Sequencing of Consensus Sequences

A modified mini alkaline lysis-PEG precipitation procedure was used to isolate plasmid DNA from positive clones. (Tartof et al., "Improved Media for Growing Plasmid and Cosmid Clones," *Bethesda Research Laboratory Focus* 9:12 (1987), which is hereby incorporated by reference in its entirety). Following the isolation procedure, DNA purity and quality was determined at 260/280 nm, and by observation of mostly supercoiled forms in agarose gel electrophoresis. Automatic DNA sequencing was performed using the ABI PRISM Ready Reaction DyeDeoxy Terminator Cycle Sequencing kit (Perkin Elmer, Foster City, Calif.) with products labeled in a Perkin Elmer Thermocycler and analyzed in an ABI 373 Genetic Analyzer (Perkin Elmer). Sequences were compared against all the sequences present in the GenBank database using the Basic Local Alignment Search Tool (BLAST) (Altschul et al., "Basic Local Alignment Search Tool," *Journal Molecular Biology* 215:403–410 (1990) which is hereby incorporated by reference in its entirety) from the National Center for Biotechnology Information.

Example 9

General Structure of α-Tubulin and PAL Genes

From GenBank sequences containing genomic DNA information, it was observed that the α tubulin gene structure varied among the few species studied (*Pisum sativum, Zea mays* and *Arabidopsis thaliana*), as well as within the species. The α tubulin gene contains between 1 and 4 introns, with sizes ranging from 83 to 1725 bp. The general structure of the α tubulin gene is shown in FIG. 1A. The only common structures are the 100 bp exon 1 and the 220 bp exon 2. For these 2 exons, a consensus region was obtained by analyzing the corresponding sequences in more abundant cDNA data present in the GenBank. FIG. 1B shows the consensus sequence for the 5' end of the α tubulin gene, corresponding to SEQ ID NO: 11. The consensus sequence contains part of exon 1, complete exon 2, and part of exon 3, and was used as template for primer design. FIG. 1C indicates the location of primers chosen from these regions of SEQ ID NO: 11.

Using the modified touchdown PCR profile described above, a 360 bp sequence from coffee was cloned and sequenced (pBSTubCof). The nucleotide sequences of pBSTubCof that are homologous to α tubulin are shown bolded in FIG. 1C. This clone contained the 3' end of exon 1 (38 bp), the complete intron 1 (110 bp), and 182 bp of the exon 2. The intron sequence does not present any similarity with other GenBank sequences, while the exon 2 sequence was 84% similar to a previously described α tubulin gene from *Prunus amygdalus* (AN: X67162), 81% similar to *Eleusine indica* (goosegrass, AN: AF008120), and 80% similar to *A. thaliana* (AN: M84697). The fragment was used as a probe in dot blots of PCR products using tobacco DNA as template, and a positive tobacco fragment was identified, cloned, and named pBSTubTob. The insert sequences of pBSTubTob that are homologous to α tubulin are shown bolded in FIG. 1D. The exon 2 contained in the tobacco fragment was 82% similar to the corresponding region in *P. amygdalus* (AN: X67162), 75% similar to *Pisum sativum* (AN: U12589), and 78% similar to *E. indica* (AN: AF008120).

The general structure of the PAL gene, shown in FIG. 2A, is more consistent among species, presenting 2 exons of approximately 400 and 1800 bp each, separated by an intron of varying size, from 91 to 1520 bp. FIG. 2B shows the consensus sequence for the 5' cDNA region of the PAL gene, corresponding to SEQ ID NO: 12, which is based on the PILEUP alignment from the sequences present in the GenBank. Primers were designed to amplify the first exon of the consensus sequence obtained after aligning cDNA sequences of homologous PAL genes. The location of the chosen primers is shown in FIG. 2B. A 203 bp PCR product from tobacco was cloned and sequenced. This is pBSPalTob, shown in FIG. 2C, which corresponds to SEQ ID NO: 13. This clone was found to be 96% similar to the corresponding region in *Nicotiana tabacum* (AN: M84466), 83% similar to *Lycopersicon esculentum* (AN: M90692), and 79% similar to *Solanum tuberosum* (AN: X63103). This clone was used as a probe to screen corresponding PCR products from coffee by dot blot, and a single positive PCR product was identified and cloned (pBSPalCof). FIG. 2D shows the pBSPalCof clone, corresponding to SEQ ID NO: 14. This 261 bp clone was 96% similar to a previously reported PAL gene from *N. tabacum* (AN: M84466), 77% similar to *L.*

*esculentum* (AN: M90692), and 78% similar to *S. tuberosum* (AN: X63103).

For exon 2, primers were designed to amplify specifically that region in the PAL B gene of *N. tabacum* reported in the GenBank (AN: AB008200). Combinations of these primers allowed the amplification of products by PCR which were finally identified by DNA sequencing, with the expected 99% similarity to the previously reported PAL B sequence.

Since the most similar sequence to coffee exon 1 was found to be that of PAL from tobacco, the primers used to amplify the exon 2 sequence from tobacco were used again in Touchdown PCR profiles for coffee. Using combinations of the primers designed for *N. tabacum,* several products were obtained when *Coffea* var. *Timor* Hybrid DNA was used as template. Southern blots of these PCR products, using the tobacco PAL exon 2 sequence as probe, allowed the identification of the corresponding sequence in coffee, and shown in FIG. 3. This 1327 bp sequence was 80% similar to the *N. Tabacum* PAL A gene (AN: AB008199), 79% similar to parsley, *Petroselinum crispum,* (AN: X81159), and 77% similar to sweet cherry, *Prunus avium,* (AN: AF036948).

Example 10

Gene Organization in Coffee Cultivars

In order to determine the gene organization, as well as possible differences between these genes in the *Coffea arabica* and *Timor* hybrid genotypes, Southern blots were performed using the cloned sequences as probes. After digesting with three restriction enzymes (BamHI, Eco RI and Hind III), the results show that the α tubulin and PAL genes are present as gene families, with 2 and 6 members, respectively. For the two genotypes, the patterns resulting from the digestion were very similar.

For the α tubulin gene, two main bands are observed when DNA is digested with every enzyme used. Hind III fragments presented molecular sizes of 4.5 and 2.5 kb, BamHI fragments were 10 kb and 6 kb long; and EcoRI fragments were 2.5 and 3.5 kb. Since the size of reported α tubulin genes is approximately 3 kb, the Southern analysis suggests that in coffee the α tubulin family has at least two members. An additional faint band was observed in the *Timor* hybrid for all the digestions (7 kb for Eco RI1; 8 kb for BamHI, and 7 kb for Hind III). Because of the high stringency used during the hybridization (62° C.), the band may be related to the tubulin family, but without a high degree of homology to the probe used.

The results from these restriction digestions suggest that the α tubulin genes are not in tandem like the α tubulin genes reported in maize (Montoliu et al., "A Tandem of Alpha-Tubulin Genes Preferentially Expressed in Radicular Tissues from *Zea mays,*" *Plant Molecular Biology* 14:1–15 (1990), which is hereby incorporated by reference in its entirety), but in two different loci. This result also contrasts with findings in plants like *Arabidopsis* (An et al., "Conserved Expression of the *Arabidopsis* ACT1 and ACT3 Actin Subclass in Organ Primordia and Mature Pollen," *The Plant Cell* 8:15–30 (1996), which is hereby incorporated by reference in its entirety) or maize (Villemur et al., "Alpha Tubulin Gene Family of Maize *Zea mays* L. Evidence for Two Ancient Alpha Tubulin Genes in Plants," *Journal of Molecular Biology* 227:81–96 (1992), which is hereby incorporated by reference in its entirety), where up to 6 α tubulin genes have been reported. The fact that few loci of α tubulin are found in coffee can indicate that the promoter sequences of these genes play a multiple functional role in the expression of the gene.

For the PAL gene, several strong bands can be observed after digesting with the three enzymes, suggesting a more complex gene family. EcoRI digestion results in seven bands with sizes 9.5 kb, 6.52 kb, 4.5 kb, 4 kb, 3.5 kb (faint), 1.2 kb, and 0.8 kb. BamHI digestion produces five bands of 11 kb, 9.2 kb, 8.5 kb, 6 kb, and 4 kb. Finally, Hind III digestion results in a very intense 9.5 kb band, and 4 more bands of 6.5 kb, 5 kb, 2 kb, and 1.5 kb. From the information on the general structure of the PAL gene, the average size of the gene is 3 kb. This would indicate that the PAL gene family consists of at least 6 members, and that is similar in the two genotypes. This number is similar to other plants where PAL families have been found (*Phaseolus vulgaris,* Cramer et al., "Phenylalanine Ammonia-Lyase Gene Organization and Structure," *Plant Molecular Biology* 12:367–383 (1989), or *A. thaliana,* Wanner et al., "The Phenylalanine Ammonia-Lyase Gene Family in *Arabidopsis thaliana,*" *Plant Molecular Biology* 27:327–338 (1995), which are hereby incorporated by reference) and contrasts with plants such as loblolly pine (Whetten et al., "Phenylalanine Ammonia Lyase from Loblolly Pine: Purification of the Enzyme and Isolation of Complementary DNA Clones," *Plant Physiology* 98:380–386 (1992), which is hereby incorporated by reference in its entirety), where only one locus of the PAL gene is present. Gene families can be associated with differential expression of the gene under different conditions; for example, specific tubulins are expressed in pollen in *Arabidopsis* (Kim et al., Pollen-Specific Expression of the *Arabidopsis thaliana* Alpha-1-Tubulin Promoter Assayed by Beta-Glucuronidase, Chloramphenicol Acetyltransferase and Diphtheria Toxin Reporter Genes," *Transgenic Research* 1:188–194 (1992), which is hereby incorporated by reference in its entirety), or different genes of the PAL family can be expressed under stimuli such as development or defense response (Bolwell et al., "L-Phenylalanine Ammonia Lyase from *Phaseolus vulgaris*: characterization and Differential Induction of Multiple Forms from Elicitor-Treated Cell Suspension Cultures," *European Journal of Biochemistry* 149: 411–419 (1985) which is hereby incorporated by reference in its entirety).

Almario, "Study of the Activity of the Phenylalanine Ammonia Lyase in the Presence of the Pathogen in Coffee Varieties Resistant and Susceptible to *Hemileia vastatrix*Ber & Br.," Universidad Nacional de Colombia, Bogota, 155 p. (1992), which is hereby incorporated by reference in its entirety, found that the basal activity of the PAL protein in coffee cultivars resistant to the coffee rust (*Hemileia vastatrix*) was higher (10.06 pkat/mg protein) than the basal activity in susceptible cultivars (3–57 pkat/mg protein). Thus, it appears that the differential activity does not depend on the presence or absence of a particular member of the PAL gene family but, perhaps, on the presence or activity of a protein factor that either activates the signal transduction mechanism that turns on the PAL gene or interacts directly with the PAL promoter.

Example 11

UP-PCR

The Unpredictable-PCR (UP-PCR) protocol, originally described by Dominguez et al., "Gene Walking by Unpredictably Primed PCR," *Nucleic Acids Research* 22:3247–3248 (1994), which is hereby incorporated by reference in its entirety, was modified and carried out as follows: 100 ng of genomic DNA were added to a PCR reaction containing 2.5 U of TaqLong DNA polymerase (STRATAGENE, La Jolla, Calif.), 1× High Salt Buffer (200 mM Tris-HCl, pH 9.2, 600 mM KCl, and 20 mM MgCl$_2$), 20 mM of each deoxynucleotide and 100 ng of the walking primer. These primers, shown in Table 4, were 19 to 29 bases long, designed originally for the amplification of other genes.

TABLE 4

| Primer 1  | caatgaacac cctagtgat g          | SEQ ID NO:15 |
|-----------|---------------------------------|--------------|
| Primer 2  | aactttctga agaggcaaga gc        | SEQ ID NO:16 |
| Primer 3  | cgggatcctc cctgtaaatt tgatgg    | SEQ ID NO:17 |
| Primer 4  | caatagcagc cacttgtgcc           | SEQ ID NO:18 |
| Primer 5  | gcaagcttca agacagtaaa gctcc     | SEQ ID NO:19 |
| Primer 6  | gtggctgcta ttgctgttag g         | SEQ ID NO:20 |
| Primer 7  | ggaattcgga aacgcttgct gggagc    | SEQ ID NO:21 |
| Primer 8  | catttgtcca tcaggctatt           | SEQ ID NO:22 |
| Primer 9  | gcaagcttcg aattgggaac gaaggaacc | SEQ ID NO:23 |
| Primer 10 | cacaacaccc aaaatcaaac c         | SEQ ID NO:24 |
| Primer 11 | actctagaag agttagctgc atgcagg   | SEQ ID NO:25 |
| Primer 12 | ctaccgccaa ctcttccacc           | SEQ ID NO:26 |
| Primer 13 | atggnttcca tgtncatgc            | SEQ ID NO:27 |
| Primer 14 | caatagcagc cacttgtgcc           | SEQ ID NO:28 |
| Primer 15 | ggaattcggt atccaggtcg gaaac     | SEQ ID NO:29 |
| Primer 16 | tttttgtttg ttgtggggt gt         | SEQ ID NO:30 |

Then, a PCR profile was performed as described in Table 5.

TABLE 5

94° C. × 5 minutes
Immediate cooling in ice

30° C. × 30 sec/35° C. × 30 sec/40° C. × 30 sec/1 cycle
45° C. × 30 sec/50° C. × 30 sec/55° C. × 30 sec/1 cycle
60° C. × 3 min/65° C. × 3 min/72° C. × 3 min/1 cycle
94° C. × 5 minutes
Addition of specific primer 94° C. × 30 sec/60° C. × 30 sec/72° C. × 4 min/6 cycles
94° C. × 30 sec/50° C. × 30 sec/72° C. × 4 min/6 cycles
94° C. × 30 sec/45° C. × 30 sec/72° C. × 4 min/6 cycles
94° C. × 30 sec/50° C. × 30 sec/72° C. × 4 min/6 cycles
94° C. × 30 sec/60° C. × 30 sec/72° C. × 4 min/6 cycles
72° C. × 5 minutes The specific primer for the reaction was primer ALP-351, which has a nucleic acid sequence corresponding to SEQ ID NO: 31 as follows:

5' gagttggagg tagggtgcc 3'

UP-PCR has the advantage of avoiding digestion and ligation steps before the PCR reaction. In the original description (Dominguez et al., "Gene Walking by Unpredictably Primed PCR," *Nucleic Acids Research* 22:3247–3248 (1994), which is hereby incorporated by reference in its entirety), UP-PCR was used only with one walking primer (WP) which was used in combination with a smaller nested primer (SWP). However, since these primers only produced a small fragment for the PAL gene, and none for the α tubulin gene, other primers present in the laboratory, already synthesized for other genes, were used as WPs, in combination with very low annealing temperatures in the PCR profile adapted for UP-PCR.

When the specific primer is added, and more stringent conditions are used for the annealing, three kinds of products are expected: the desired sequence, fragments resulting from self priming of the walking or the specific primer, and unspecific products amplified with the pair of primers used. For this reason, it is always necessary to perform a Southern blot in order to identify the correct one. PCR products obtained with the TaqLong mixture (Stratagene's Taq DNA polymerase plus Pfu DNA polymerase) were not only longer than those normally obtained with Taq polymerase (up to 10 kb, compared to 5 kb or less), but also more robust. This avoided the need to run a second PCR reaction with the products of the initial reaction in order to obtain enough DNA to be detected in the gel by staining with ethidium bromide, which was usually the case when plain Taq was used.

Example 12

α Tubulin Promoter UP-PCR

Figure 4B:
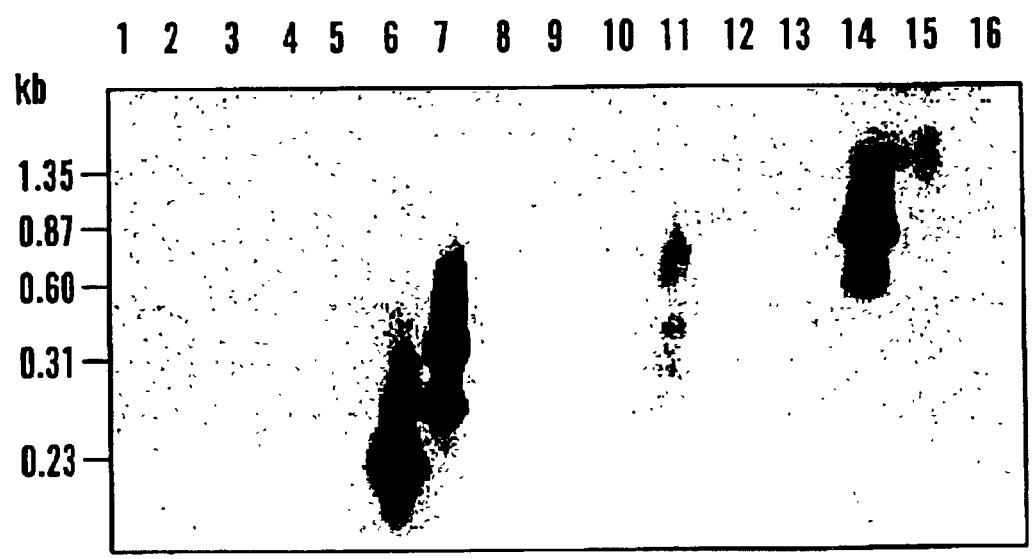

The upstream sequence of the α tubulin gene was cloned using the modification of UP-PCR described in Example 5. Three out of 16 walking primers used produced a clear positive result in the Southern blot, as shown in FIG. 4. Positive products are observed with walking primers 6, 7, 11, and 14. However, only the 1.5 kb product generated using walking primer 14 was long enough to contain new significant sequence information, i.e., a putative promoter.

Example 13

Analysis of *Coffea* α Tubulin Promoter

FIGS. 5A–B show the analysis of the *Coffea* α tubulin promoter. The UP-PCR product from the reaction with walking primer 14 was cloned (pBSPrtubCof) and found to be 1,670 bp long, corresponding to SEQ ID NO: 1. The 330 bp sequence close to the 3' end (specific primer) was 100% identical to the clone pBSTubCof, described above in Example 9. An open reading frame was identified starting at the ATG triplet in base 1286. This marks the beginning of exon 1, which extends until base 1378 (coding for 31 amino acids) and that is 91% similar to the same region in *Eleusine indica* (goosegrass, Accession Number AF08120), 88% similar to *Zea mays* (AN: X61379), and 90% similar to *Prunus amygdalus* (AN: X67162). The remaining 1286 bp correspond to the upstream sequence of that gene. Other than the 5 Transcription Factor II D boxes (TFIID) and the yeast transcription factor located in front of the ATG initiation codon of the α tubulin gene, no homology was found for the rest of the upstream sequence in the GenBank or TRANSFAC databases. The only donor and acceptor splicing sites found corresponded to positions 1379 and 1485 which match the location of intron 1, identified previously from the similarity with the structure of α tubulins from other plants.

Using the Transcription Element Search Software (TESS), it was found that the region between positions 962 and 991 contained 5 motifs associated with the Transcription Factor IID (TFIID): TTCAAA from mouse (Tamura et al., "Core Promoter of the Mouse Myelin Basic Protein Gene RT Governs Brain-Specific Transcription In Vitro," *EMBO* 9:3101–3108 (1990), which is hereby incorporated by reference in its entirety), AGTTCA from rat (Drouin et al., "Glucocorticoid Receptor Binding To A Specific DNA Sequence Is Required For Hormone-Dependent Repression of Pro-opiomelanocortin Gene Transcription," *Molecule Cell Biol* 9(12) 5305–14 (1989), which is hereby incorporated by reference in its entirety in its entirety), and GCCAGCTGG from rat (Hu et al., "HEB, a Helix-Loop-Helix Protein Related to E2A and ITF2 that can Modulate the DNA-Binding Ability of Myogenic Regulatory Factors," *Molecular and Cellular Biology* 12:1031–1042 (1992), which is hereby incorporated by reference in its entirety). TFIID is the complex formed by the TBP (TATA Binding Protein) and different TAFs (TATA Activator Factors) which are involved in core promoter recognition and recruitment of the complex RNA Pol II-TFIIF (Roeder, "The Role of Initiation Factors in Transcription by RNA Polymerase II," *Trends in Biochemical Science* 21:327–335 (1996), which is hereby incorporated by reference in its entirety).

The analysis with SignalScan is shown in FIGS. 5A–B. The presence of another TATA box is revealed at position 316. Visual inspection shows a CAAT box at 215, and using MapDraw (DNAStar, LASERGENE, Madison, Wis.) a potential open reading frame is observed from 361 to 576 (72 amino acids). This potential open reading frame did not show any similarity to any known sequence in the GenBank.

In addition, visual inspection of the sequence, shown in FIGS. 5A–B, reveals three palindromic motifs present at positions 149 (agtaattaaattact), 883 (agtttaaact), and 990 (aaatcatttt) of SEQ ID NO: 1. One direct repeat at 860 (gcccaggcccca), and 23 boxes of (aaaa) tetrads. Palindromic motifs have been associated with the binding site of dimeric transcription factors and motifs (Griffiths et al., *An Introduction to Genetic Analysis*, Fifth Edition., New York: W. H. Freeman and Company (1993), which is hereby incorporated by reference in its entirety). Spaced runs of A-Ts can cause a local bending of DNA, and bending of the upstream region in a promoter has been observed to influence promoter activity (Travers, "DNA-Protein Interactions," St. Edmundsbury Press, Bury St. Edmunds, Great Britain (1993), which is hereby incorporated by reference in its entirety).

The position of the sequence with respect to the open reading frame, as well as the presence of characteristic transcription initiation elements supports the possibility that a putative promoter for the α tubulin gene of coffee was cloned.

Example 14

Screening of Genomic Library for PAL Gene

An amplified genomic library made with *C. arabica* DNA partially digested with Sau3AI and cloned in Lambda GEM-11 (Promega), with an insert average size of 20 kb (Chaparro, "Construction of a Genomic Library of *C. arabica* cv. Caturra," Universidad Nacional de Colombia, Bogota, 81 p (1993), which is hereby incorporated by reference in its entirety), and a phage titer of 75000 pfu/μl, was plated in 22×22 cm plates (NUNC, Rochester, N.Y.) containing 250 ml of LB bottom agar.

For every plate, 300 μl of the host bacteria *E. coli* LBE 322, grown overnight in LB medium supplemented with 0.2% maltose and 10 mM $MgSO_4$, was infected with 1 μl of the amplified library and incubated for 30 minutes at 37° C. Then, 50 ml of molten top agarose was added to the bacterial suspension and immediately poured over the plates. After incubation for 8 hours at 37° C., final plaque densities were between 150 and 200 pfu per square centimeter. In order to screen five times the genomic content of *C. arabica*, six plates were used, containing a total of 420,000 plaques.

Plates were kept at 4° C. for at least 1 hour in order to harden the top agarose before 20×20 cm nylon membranes (GeneScreen Plus, NEN) were placed down for 1 to 2 minutes to lift the plaques. Denaturation of DNA was carried out by placing the membranes on a Whatman 3 MM paper sheet saturated with denaturing solution (0.2 M NaOH and 1.5 M NaCl) for 2 minutes. Membranes were then moved over Whatman paper soaked with neutralization solution (0.4 M Tris-HCl, pH 7.6 and 2×SSC) for 2 minutes, and finally rinsed with 2×SSC for 2 minutes.

The probe used consisted of a 1311 bp PCR product containing the exon 2 sequence of the *C. arabica* PAL gene, shown in FIG. 3. The labeling reaction was carried out by using random oligonucleotide primers (Sambrook et al., "Molecular Cloning: A Laboratory Manual (Second Edition)," Cold Spring Harbor, N.Y., Cold Spring Harbor Laboratory Press (1989), which is hereby incorporated by reference in its entirety); 28 μl containing 50 ng of template were denatured by incubation at 100° C. for 10 minutes and immediately put on ice. Then, 11 μl LS buffer, 4 μl Bovine serum albumin, 1 U of Klenow fragment (Promega), and 4 μl of $^{32}P$ [α-dATP] (NEN, Boston, Mass.) were added to the tube and incubated at 37° C. for 1 to 2 hours. After this, the probe was denatured by incubation for 10 minutes at 100° C., followed by placing the tube on ice.

Dry membranes were incubated at 65° C. in prehybridization solution (50% Dextran sulfate, NaCl, and SDS) for 2 hours, before adding the denatured probe, and hybridized for 12 hours. Membranes were then washed with 2×SSC at room temperature for 5 minutes, 2×SCC, and 0.1% SDS at 65° C. for 15 minutes, and 1×SSC and 0.1% SDS at 65° C. for 15 minutes. Probe-positive plaques were plugged out with a borosilicate Pasteur pipet, and resuspended in 100 μl of SM buffer (0.01% Gelatin, 50 mM Tris-HCl pH 7.5, 100 mM NaCl, and 8 mM MgS04) to be submitted to secondary and tertiary screenings in 100 mm Petri dishes before phage DNA was purified with the Wizard Lambda Preps DNA Purification System (Promega), and subcloned into pBluescript II SK-(Stratagene) using standard techniques (Sambrook et al., "Molecular Cloning: A Laboratory Manual (Second Edition)," Cold Spring Harbor, N.Y., Cold Spring Harbor Laboratory Press (1989), which is hereby incorporated by reference in its entirety).

Example 15

Identification of PAL Promoter from *C. arabica* Genomic Library

After the third round of purification as described above (Example 14), nine recombinant phages were obtained from the C. arabica library and amplified for restriction digestion analysis. A 6 kb BamHI fragment from a single recombinant phage, identified during Southern blots performed with the PAL exon 2 probe, was chosen for subcloning and subsequent sequence analysis. Partial sequencing of this fragment generated information for a 0.9 kb region corresponding to the 5' flanking region of the PAL gene (putative promoter), which has a nucleic acid sequence corresponding to SEQ ID NO: 2.

As seen in FIGS. 6A–C, the promoter sequence is followed by the complete exon 1 (387 bp) and intron 1 (2.6 kb), and the 5' end of the exon 2 (530 bp). Intron 1 did not show any significant similarity to any other sequence present in the GenBank release 102. Searches for splicing sites indicate the presence of three donor sites in exon 1 (positions 1090, 1138, and 1315), and two acceptors located in exon 2 (positions 3170 and 3621). Although there is a possibility of alternative splicing between the different donors and acceptors, from cDNA information present in the GenBank, it can be concluded that intron 1 is located between positions 1315 and 3621 in all the plants studied.

Analysis of the putative promoter using the programs SignalScan and MatInspector is shown in FIGS. 6A–C, indicating the presence of two recognition sites for transcription factors. As shown in FIG. 6A, the sequence GGTTTTTAATA, starting at position 361 of SEQ ID NO: 2, is associated to the transcriptional silencer SBF-1, which interacts in the promoter region of the Chalcone synthase gene (Lawton et al., "Silencer Region of A Chalcone Synthase Promoter Contains Multiple Binding Sites For A Factor, SBF-1, Closely Related to GT-1," *Plant Mol. Biol.* 16:235–249 (1991) which is hereby incorporated by reference in its entirety).

Also, three boxes (TCCGACCAC, GCCGACCTG, and AGCTACCAT) found at positions 691, 731, and 1050, are related to the transcription factor B-myb, which is involved in the flavonoid biosynthesis pathway (Grotewold et al., "The myb-homologous P Gene Controls Phlobaphene Pigmentation in Maize Floral Organs by Directly Activating a Flavonoid Biosynthetic Gene Subset," *Cell* 76:543–533 (1994), which is hereby incorporated by reference in its entirety).

The presence of the elements associated with these transcription factors agree with the role of the PAL protein in the synthesis of cinnamic acid, which feeds several biosynthetic routes that lead to the production of phenylpropanoid-derived products. Chalcone synthase (CHS) is another plant enzyme closely involved in this role. These secondary products, generated from PAL activity, are required in processes including xylem development, petal pigmentation, intracellular signaling, UV protection and plant defense (Hahlbrock et al., "Physiology and Molecular Biology of the Phenylpropanoid Metabolism," *Annual Review of Plant Physiology and Plant Molecular Biology* 40:347–369 (1989), which is hereby incorporated by reference in its entirety).

In contrast to the α tubulin putative promoter, there is not a well defined TATA box in this particular PAL promoter, although there is a potential candidate in the sequence between positions 752 and 765. This suggests that the 5' untranslated RNA (UTR) region is contained in the 200 bp sequence following this motif. However, as in the α tubulin promoter, several spaced runs of A-Ts are also observed in the PAL promoter, although with less frequency.

Example 16

Cloning of PAL Promoter from Tobacco for Transient Expression of uidA

Based on the sequence of the PAL gene from tobacco (AN: M84466) forwarded to the GenBank database by T. Fukasawa Akada (1991), which is hereby incorporated by reference in its entirety, two primers were designed with the PRIMERSELECT computer software (DNAStar, LASERGENE, Madison, Wis.) in order to amplify the promoter sequence of that gene. Forward primer Pal 29, SEQ ID NO: 32, (5' caaagccgcc gaagtgat 3') and reverse primer Pal 94, SEQ ID NO: 33, (5' agcagccact tgtgccactg 3') amplified a 1,924 bp PCR product that was blunt-end cloned into the EcoRV site of pBluescript. After sequencing, the construct was designated pBSPrPALTob.

Example 17

Engineering of Promoter Sequences into pBI101

Figure 7A:
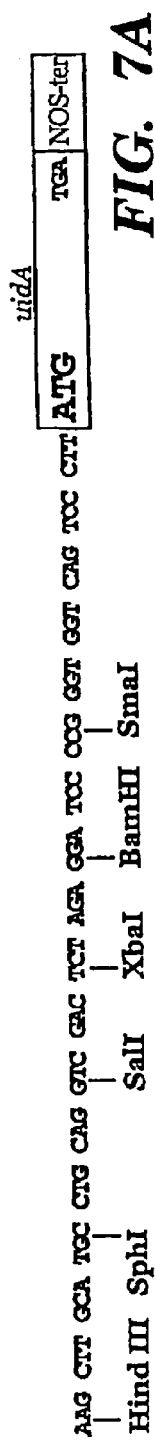
FIGS. 7A–E are maps of constructs used for transient expression experiments.
Figure 7B:
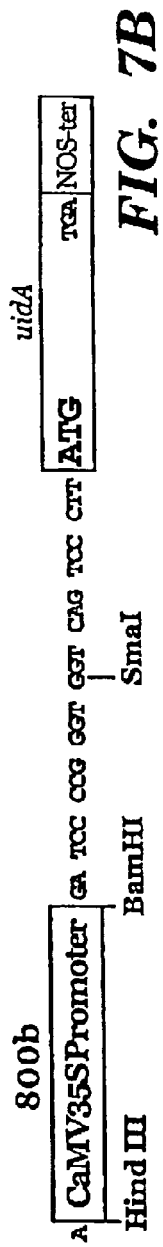

The large scale plasmid preparation protocol described by Sambrook et al., "Molecular Cloning: A Laboratory Manual (Second Edition)," Cold Spring Harbor, N.Y., Cold Spring Harbor Laboratory Press (1989), which is hereby incorporated by reference in its entirety, was used to isolate plasmid DNA for use in vector construction. Vectors pBI101 (promoter-less) and pBI121 (CaMV35S promoter) were purchased from Clontech (Palo Alto, Calif.) The multicloning region of the pBI101 vector is shown in FIG. 7A. FIG. 7B shows the multicloning region of pBI121. Four other promoters were cloned between the Hind III and BamHI sites present in the multicloning site of the plant expression vector pBI101 in order to control the expression of uidA.

Figure 7C:
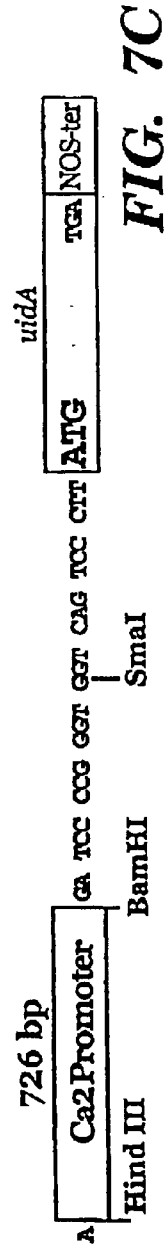
Figure 7D:
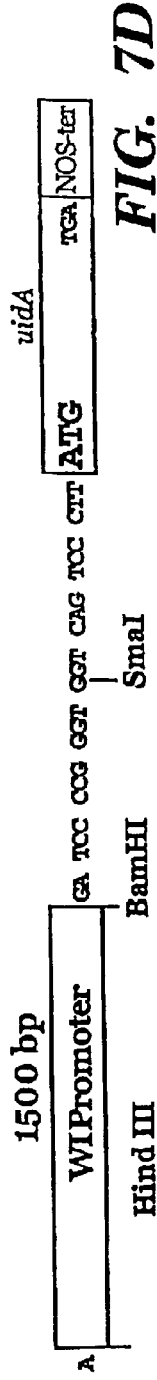
Figure 7E:
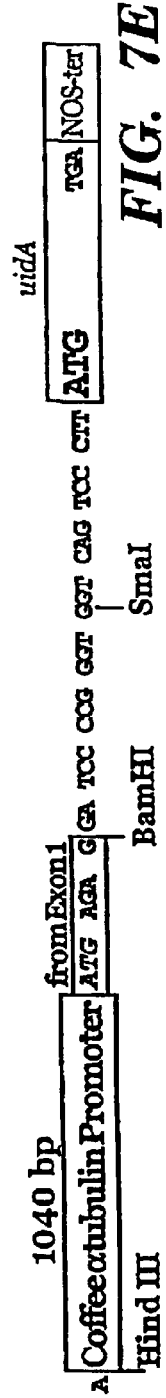
Figure 8:
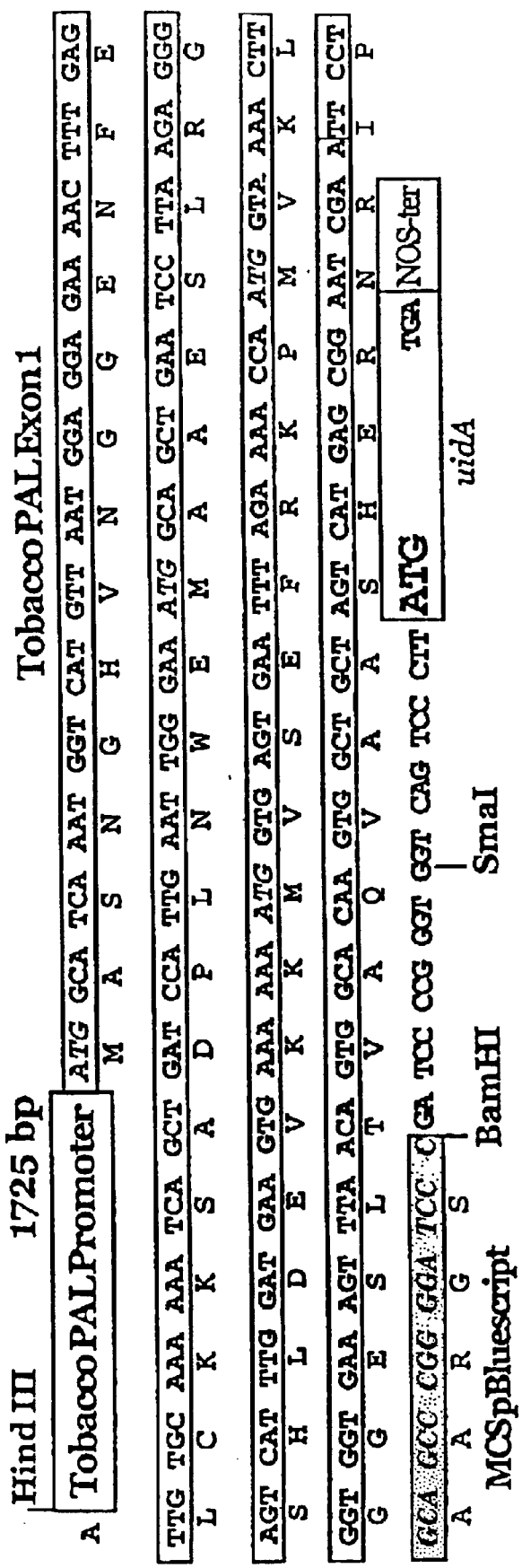
FIG. 8 is map of the pBIPAL vector (SEQ ID NO: 50). A 1725 bp segment of the tobacco PAL gene, and a 201 bp from exon 1 of the PAL gene were cloned in front of (5' to) the uidA gene. Three ATG initiation codons are present in the exon 1 sequence, all in-frame with the uidA initiation codon. The resulting fusion protein (SEQ ID NO: 51) is indicated below the nucleotide seciuence.
Figure 9A:
FIGS. 9A–G show expression of the uidA gene in coffee and tobacco tissue after bombardment with DNA coated tungsten particles. Samples were incubated at 25° C. for two days after bombardment, treated with X-Gluc solution overnight at 37° C. and cleared with 75% ethanol for 24 hours.
Figure 9B:
Figure 9C:
Figure 9D:
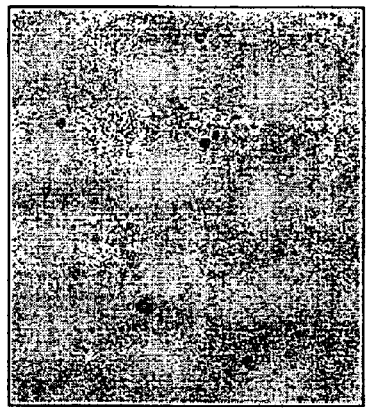
Figure 9E:
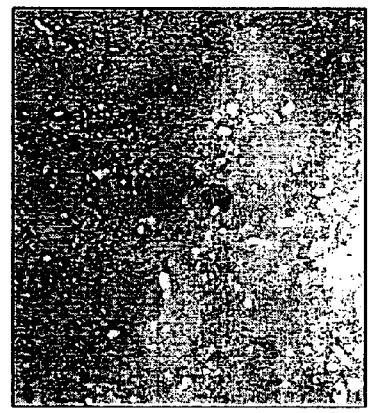
Figure 9F:
Figure 9G:

The Ca2 promoter contained 726 bp and was subcloned from pCa2C38/121 by digestion with Hind III and Bg1 II to create vector pBICa2, shown in FIG. 7C. FIG. 7D shows the construct pBIWI, with the wound inducible promoter from potato ("WI" promoter) inserted. This vector consists of a 1.5 kb sequence removed from the vector pWIAtt/121 by digestion with Hind III and BamHI. The coffee α tubulin promoter was subcloned from pBSPrtubCof by amplifying a 1047 bp fragment with the forward primer ATUB-262, SEQ ID NO: 34, (5' cccaagcttc gcttttgtct gccttagtat g 3') that contains a Hind III site on the 5' end, and the reverse primer ATUB-1033, SEQ ID NO: 35, (5' cgggatcctc tcattttcgc gatgttttga g 3') that contains a BamHI site on the 5' end. The PCR product was purified, digested with Hind III and BamHI, and moved into pBI101. The pBαtub construct, shown in FIG. 7E, encodes a fusion protein that contains the first 2 amino acids from the coffee α tubulin exon 1, followed by 8 amino acids encoded by the pBI101 multicloning site, and then the complete GUS coding region. The tobacco PAL promoter was subcloned from pBSPrPALTob by digestion with Hind III and BamHI and inserted in pBI101 to create pBIPAL, shown in FIG. 8. A resulting fusion protein encoded 67 amino acids from PAL exon 1, 19 amino acids from the pBS vector, 8 amino acids from the multicloning site of pBI101, and then the uidA gene.

Example 18

Particle Bombardment

For the delivery of DNA using particle bombardment, the protocol described by Kikkert, "The Biolistic PDS-1000/He Device," *Plant Tissue and Organ Culture* 33:221–226 (1993), which is hereby incorporated by reference in its entirety, was followed. Before bombardment, 60 mg of M-10 tungsten particles (1 μm average diameter, GTE Products Corporation, Towanda, Pa.) were sterilized by immersion in 70% ethanol, vortexed, and incubated for 15 minutes. Particles were then pelleted by centrifugation at 13,000 g for 5 minutes, resuspended in 1 ml of sterile Type I water, and centrifuged again. This water wash was repeated three times, after which the particles were resuspended in 1 ml of 50% sterile glycerol solution.

In order to adsorb DNA to microparticles, 50 µl of the particle suspension were aliquoted into a microcentrifuge tube, and very quickly 5 µl of 1 ug/µl plasmid DNA, 50 µl of 2.5 mM $CaCl_2$ and 20 µl of 0.1 M spermidine were added in succession with frequent vortexing. The microtubes were then placed on a vortex shaker for 10 minutes, after which the particles were precipitated by centrifugation at 13,000 g for 5 seconds. The pellet was rinsed once with 140 µl of 70% ethanol, once with 140 µl 100% ethanol, and finally resuspended in 48 µl of 100% ethanol. Afterwards, microtubes were dipped for 3 seconds in an ultrasonic cleaner to allow the particles to disperse. 6 µl of DNA coated particles was pipetted onto the center of a Kapton membrane (DuPont, Wilmington, Del.) and dried in desiccant filled Petri dishes.

*Nicotiana tabacum* NT1 cell cultures were provided by J. Kikkert in Dr. John Sanford's laboratory (Cornell University). Tissue culture seedlings and somatic embryos of *Coffea arabica* cv. Colombia genotype BK620 were provided by C. Gongora in Dr. Roxanne Broadway's laboratory (Cornell University). Plant tissue was placed on RMO medium (xMS salts, 1xMS vitamins, 0.5 mg/l benzyladenine (BA), 2 mg/l indole acetic acid (IAA), 3% sucrose and 0.9% agar) in petri plates, and in the case of cell cultures, on top of sterile Whatman No. 1 filter paper on RMO plates.

A prototype of the Biolistic PDS-1000/He device (BioRad, Hercules, Calif.) was set to 1100 psi helium pressure, 28 inches of mercury vacuum level, and 12 cm. of particle flight distance, and operated according to the instructions (Kikkert, "The Biolistic PDS-1000/He Device," *Plant Tissue and Organ Culture* 33:221–226 (1993), which is hereby incorporated by reference in its entirety). After two consecutive bombardments, the tissue was incubated for two days under cool fluorescent light (16 hr photoperiod, 50–60 µmoles/m$^2$s) at 25° C., and, then, analyzed for GUS expression.

All the constructs, except for pBI101, were able to drive the expression of GUS in the bombarded tissues, although with some differences. FIG. 9 shows the expression of the uidA gene in coffee and tobacco tissue after particle bombardment. A part from the variation in the particle distribution from plate to plate caused by the bombardment process itself, it was evident that the number of blue spots observed was less frequent with the PAL promoter from tobacco than with the other constructs, regardless of the tissue used. In tissues like tobacco cell cultures and coffee seedlings and tobacco leaves, the blue spots formed after the X-Gluc treatment were generally limited to the area around the microprojectile entry place. However, in coffee embryos, the X-Gluc treatment tended to show a more diffuse pattern.

In coffee, results of bombardment of greenhouse leaves were difficult to see because of the accumulation of phenolics that turned the tissues brown during the X-Gluc incubation. This browning persisted after adding 0.02% mercaptoethanol to the histochemical reaction. The problem was overcome with the bombardment of leaves and stems from tissue culture seedlings. Also, no blue color developed when the promoter-less construct pBI101 was used, except on coffee embryos, which showed a light blue coloration. This reaction has been reported previously by Boxtel et al., "Transient Expression of β-Glucuronidase Following Biolistic Delivery of Foreign DNA into Coffee Tissues," *Plant Cell Reports* 14:748–752 (1995), which is hereby incorporated by reference in its entirety, during particle bombardment of *C. arabica* cv. Caturra, and it is presumed to be due to endogenous glucuronidase activity in the embryos, which also occurs in embryos from other plant species (Hu et al., "HEB, a Helix-Loop-Helix Protein Related to E2A and ITF2 that can Modulate the DNA-Binding Ability of Myogenic Regulatory Factors," *Molecular and Cellular Biology* 12:1031–1042 (1992), which is hereby incorporated by reference in its entirety). Here, as can be observed in FIG. 9, in embryos of the same age, the tubulin promoter shows a much stronger reaction than the pBI101 or even the double CaMV35S. Table 6 presents a summary of uidA qualitative gene expression in tobacco and coffee tissues, after particle bombardment with pBI1011 based constructs.

TABLE 6

| Tissue | pBI construct | | | | |
|---|---|---|---|---|---|
| | 101 | 121 | Ca2 | WI PAL | αtub |
| Tobacco greenhouse leaves | − | + | + | + ±[1] | + |
| Tobacco cell culture | − | + | + | + + | + |
| Coffee somatic embryos | −[2] | + | + | + + | + |
| Coffee tissue culture seedlings | − | + | + | + − | + |

[1]GUS expression is very low.
[2]Background glucuronidase activity is observed.

Results from the transient expression experiments confirmed that the upstream sequence cloned from the Timor hybrid actually behaves as a promoter. This test was necessary, since some plant genes are known to have long 5' UTR's sequences (700 bp, Chang et al., "Cloning of a cDNA for a Chitinase Homologue which Lacks Chitin-Binding Sites and is Down-Regulated by Water Stress and Wounding," *Plant Molecular Biology* 31:693–699 (1996), which is hereby incorporated by reference in its entirety) that although they are involved in the regulation of transcription initiation, are not capable of driving gene expression by themselves.

Example 19

Protoplast Preparation

Coffee cell cultures were initiated from secondary embryogenic tissue of *C. arabica* genotype BK 620 provided by M. Aponte at CENICAFE (Chinchiná, Colombia), at a density of 5 mg/ml of Medium 2 (0.5xMS salts, 1xB5 vitamins, 37 mg/ml cystein, 1 mg/ml BAP, 30 g/l sucrose, pH 5.7). After 3 weeks, tissue was decanted and treated with a solution containing 1% cellulase R10, 0.8% macerozyme and 0.5% driselase, dissolved in K3 salts containing 0.4 M sucrose, 0.25 g/L xylose, 0.25 g/l MgS04, 0.25 g/l $KN0_3$, and 50 mg/l cystein, according to the description of Grezes et al., "Factors Influencing Protoplast Isolation from *Coffea arabica* Cells," *Plant Cell, Tissue and Organculture* 36: 91–97 (1994), which is hereby incorporated by reference in its entirety. Tobacco protoplasts were obtained from greenhouse leaves disinfected by immersion in a solution of 10% of commercial sodium hypochlorite and 0.05% SDS for 20 minutes, then washed twice for 5 minutes in distilled sterile water and finally dried on a sterile paper towel. Leaf tissue was then treated overnight with isolation medium (1xKM salts, 1x Nitsch & Nitsch vitamins, 0.4 M sucrose, 0.25 g/l xylose, 0.45 gM 2,4-D, 5.38 µM NAA and 1 gM BAP, pH 5.8) containing 1.25% cellulase R10 and 0.4% macerozyme.

For both plant tissues, after overnight incubation at 28° C., protoplasts were filtered through a 50 mm mesh diameter screen and pelleted by centrifugation at 1000 rpm for 10 minutes in a free angle rotor, without applying brakes. Protoplasts were resuspended in 13 ml of isolation medium and 1 ml of W5 solution (154 mM NaCl, 125 mM $CaCl_2$, 5 mM KCl, 5 mM glucose, pH 5.6) was laid on top of the tube. After spinning at 800 rpm for 5 minutes, the layer of protoplasts at the interphase was recovered and transferred to new tubes. Protoplasts were washed once with 10 ml of W5 solution and the concentration was adjusted to $10^6$ protoplasts/ml with MaMg solution (0.5M mannitol, 15 mM $MgCl_2$, 0.1% MES (morpholinoethane sulphonic acid, pH 5.6) after counting with a hemacytometer. Protoplast viability was determined by staining 10 μl of protoplasts with 2 μl of 4% trypan blue. Only protoplast preparations with at least 80% viability were used for transformation.

Example 20

Protoplast Transformation

One ml of protoplast solution containing $10^6$ protoplasts was heated to 45° C. for 5 minutes and then cooled to room temperature for 10 minutes. Then, 10 μg of DNA was added, mixed, and incubated with protoplasts for 10 minutes. One volume of 40% PEG 4000 in MaMg solution was added to the protoplasts drop by drop and the solution was incubated for 30 minutes. The mixture was diluted with W5 medium to a final volume of 14 ml and protoplasts were spun down and resuspended with NT1 protoplast culture medium to a final density of $5 \times 10^5$ protoplasts/ml. For evaluation, protoplasts were incubated for 2 days, in the dark at room temperature, centrifuged, and resuspended in 100 μl of MUG assay buffer (50 mM $Na_2HPO_4$ pH 7.0, 0.1% SDS, 10 mM $Na_2$ EDTA, 10 mM β-mercaptoethanol), then macerated with a motor driven Kontes, and sonicated with 10 pulses of 3 seconds for a total of 30 seconds. Finally, disrupted protoplasts were centrifuged at 16,000 g for 10 minutes and the supernatant was saved for analysis.

Example 21

Polyethylene Glycol Transformation of Tobacco

Coffee protoplasts could not be used for transformation experiments, because the yields from the established cell cultures were in the order of $10^3$ per gram of fresh tissue, which is out of the practical range to perform the experiments.

In contrast, yields from tobacco leaves were on the order of $10^5$ to $10^6$ protoplasts per gram of fresh tissue, therefore this material was used exclusively for the polyethylene glycol (PEG) transformation experiments. One common factor during the evaluations of GUS activity from tobacco protoplasts was the background activity present even in controls without any DNA treatment. Jefferson indicates that this background activity can be due to the residual presence of the enzymes used to remove the cell wall, which can have significant β-glucuronidase activity. (Jefferson, "Assaying Chimeric Genes in Plants: The GUS Gene Fusion System," *Plant Molecular Biology Reporter* 5:387–405 (1987) which is hereby incorporated by reference in its entirety.)

Also, endogenous β-glucuronidase activity associated with cell wall synthesis can occur, since improved transient expression has been observed after adding 2,6 DB, an inhibitor of cell wall synthesis, to the protoplast cultivation medium (Chapel et al., "Temporary Inhibition of Cell Wall Synthesis Improves the Transient Expression of GUS Gene in *Brassica napus* Mesophyll Protoplasts," *Plant Cell Reports* 9:105–108 (1990), which is hereby incorporated by reference in its entirety).

GUS expression from PEG transformation varied greatly among experiments, which may be due to the quantification of small amounts of proteins extracted from the protoplasts, or the physiological conditions of the leaves in the greenhouse. Table 7 shows GUS activity in tobacco protoplasts two days after PEG transformation.

TABLE 7

| | Construct Experiment | | | | |
|---|---|---|---|---|---|
| Construct | I | II | III | IV | V |
| Control | 150 | 85 | 102 | 73 | 185 |
| pBI101 | 146 | 104 | 125 | 65 | 187 |
| pBI121 | 256 | 127 | — | 86 | 218 |
| PBIWI | — | 135 | 143 | — | 244 |
| pBIPAL | 308 | 121 | 142 | 97 | 207 |
| pBITub | 300 | 125 | 147 | 120 | 299 |
| pBICa2 | 511 | 150 | 233 | 182 | 420 | a. GUS activity in pmol 4-MU/minute/mg of protein.

In order to compare the replications, a relative strength was calculated by removing the background amount, represented in the control sample, from all the samples, and dividing the data with the smallest value in the column. As Table 8 demonstrates, these results are consistent that the expression with the double CaMV35S promoter (pBICa2) was the strongest among all the constructs evaluated. Relative promoter strength is corrected for background activity in Table 8.

TABLE 8

| | Relative Strength | | | | |
|---|---|---|---|---|---|
| Construct | I | II | III | IV | V |
| pBI121 | 1.00 | 1.16 | | 1.00 | 1.50 |
| pBIM | — | | 1.38 | 1.02 | 2.68 |
| pBIPAL | 1.49 | 1.00 | 1.00 | 1.84 | 1.00 |
| pBITub | 1.41 | 1.11 | 1.12 | 3.61 | 5.18 |
| pBICa2 | 3.40 | 1.80 | 3.27 | 8.38 | 10.68 |

Transient expression can give information about the effectiveness of the construct to express a transgene, since problems related with the promoter, the frame-shift, or even codon preference can be detected before results from a longer stable transformation experiments can be observed. However, transient expression suffers from certain limitations. The introduced promoter maybe acting in an altered manner since it can be present in high copy numbers, it is not subjected to the higher order of the chromosome organization, and it can be interacting with repressors or activators under circumstances different from normal physiological conditions. For this reason, stable transformation experiments must be carried out to further characterize a promoter sequence.

Example 22

*Agrobacterium* Transformation for Stable Expression of uidA

To prepare competent cells, *Agrobacterium tumefaciens* LBA 4404 were grown in 20 ml of LB medium at 28° C. for 2 days, cells were cooled down in ice for 30 minutes and then collected by centrifugation at 4,500 rpm for 15 minutes. Cells were washed twice with 50 ml of ice cold sterile water, once with 20 ml of 10% ice cold glycerol, and finally resuspended in 2 ml of 10% glycerol. For electroporation, 40 µl of competent *Agrobacterium* cells were incubated with 1 µl of DNA (approximately 500 ng) and placed in a 0.2 cm gap electroporation cuvette. The cuvette was placed in the Gene Pulser electroporation apparatus (BioRad, Hercules, Calif.) and subjected to a current of 2.5 kV for 3 to 4 milliseconds, with a resistance of 200 ohms and capacitance of 25 µFD. Immediately, 460 µl of SOC medium was added to the cuvette, and contents transferred to Falcon tubes. Tubes were incubated at 28° C. for 1 hour and 200 µl of cells were plated in LB medium plates containing 75 µg/ml of kanamycin. Plates were incubated for 24–48 hours at 28° C., and colonies were transferred to new plates. After 24 hours, colonies were subjected to a colony PCR screening in order to confirm the presence of the plasmid. Positive colonies were grown in 20 ml of LB medium containing 75 µg/ml of kanamycin. After 48 hours, cells were diluted in 1 volume of Simplified Induction Medium (SIM) (Alt-Moerbe et al., "Differences in Induction of Ti Plasmid Virulence Genes virG and virD and Continued Control of virD Expression by Four External Factors," *Molecular Plant-Microbe Interactions* 2:301–308 (1989), which is hereby incorporated by reference in its entirety), and placed in an empty Petri dish for leaf transformation.

Example 23

Tobacco Leaf Explant Transformation

Young tobacco leaves from greenhouse plants were surface sterilized by immersion in a solution of 10% of commercial sodium hypochlorite (Clorox) and 0.05% SDS for 20 minutes, washed twice for 5 minutes in distilled sterile water, and finally dried on a sterile paper towel. Discs 1.1 cm in diameter were cut from the leaves using a cork borer and placed in the Petri dishes containing SIM and the *Agrobacterium* for a few seconds. Leaf discs were then dried on paper towels and placed on Petri dishes containing RMO medium without antibiotics. Plates were incubated under periodic light conditions, and, after three days, discs were transferred to RMO containing 300 mg/ml of kanamycin and 300 mg/ml of carbenicillin. These plates were incubated for four weeks until shoots were observed. Shoots were then removed, cleaned of any surrounding callus tissue, and transferred to Magenta boxes containing RMO medium without hormones, but with kanamycin and carbenicillin. After 2 weeks, when roots were observed, shoots were taken out of the Magenta boxes and the roots were washed to remove the agar. Seedlings were then planted in individual pots and covered immediately with a plastic bag. After three days, the tips of the bag were cut with scissors, and three days later the bags were removed completely.

Example 24

PCR Verification for Transformants

DNA from fully rooted plants selected in rooting medium containing kanamycin was isolated using the miniprepation method described above. PCR reactions were performed to verify the absence in plant DNA of the virG gene present in the disarmed tumor inducing plasmid (pTI) of *A. tumefaciens* (Chen et al., "Characterization of the Super-virulent virG Gene of the *Agrobacterium tumefaciens* Plasmid pTiBO542," *Molecular and General Genetics* 230:302–309 (1991), which is hereby incorporated by reference in its entirety). For this, primers VIR-F (5' gccggggcga gaccatagg 3') SEQ ID NO: 36, and VIR-R (5' cgcacgcgca aggaacc 3') SEQ ID NO: 37 were used, and the presence of a 1000 bp band was an indication of *Agrobacterium* contamination.

In addition, for each construct, a pair of primers were chosen to amplify a region of the T-DNA containing the promoter and the uidA gene. For the promoter-less construct (pBI101) the primers GUS-F (5' tagcgggact ttgcaagtg 3') SEQ ID NO: 38, and GUS-R1063 (5' cagcagcagt ttcatcaatc a 3'), SEQ ID NO: 39 were used to amplify the uidA gene generating a PCR product of 1000 bp. For the pBICa2 vector, primers 35S-F (5' cccactatcc ttcgcaagac 3'), SEQ ID NO: 40, and GUS-R1063 produced a PCR band of 1273 bp. For pBIPAL, primers PAL-29 (5' caaagccgcc gaagtgat 3'), SEQ ID NO: 32, and GUS-R1063 produced a 3068 bp PCR product. Finally, for pBIatub, primers ATUB-262 (5' cccaagcttc gcttttgtct gccttagtat g 3'), SEQ ID NO: 34, and GUS-RI063 generated a 2144 bp product.

Example 25

GUS Histochemical Assay

Tissue was placed in Falcon 12 cuvette multiwell tissue culture plates (Becton Dickson, Lincoln Park, N.J.), containing X-Gluc solution (0.1 M phosphate buffer, 5 mM potassium ferrocyanide, 5 mM potassium ferricyanide, 0.1% Triton X100, and 1 mg/ml of 5-bromo-4-chloro-3-indolyl-p-D-glucuronic acid) (X Glue) in NN-dimethyl formamide) and vacuum treated for 30 seconds at 200 mTorr (1 Torr=1 mm Hg). The plates were incubated overnight at 37° C., after which the X-Gluc solution was first replaced by 70% ethanol for 2 hours, and then replaced by 95% ethanol to clarify the tissue.

Example 26

GUS Quantitative Fluorometric Assay

This protocol is based on the fluorometric assay described by Jefferson et al., "Assaying Chimeric Genes in Plants: The GUS Gene Fusion System," *Plant Molecular Biology Reporter* 5:387–405 (1987) which is hereby incorporated by reference in its entirety. For every sample, 55 µl of 2 mM methyl umbelliferyl glucuronide (MUG) solution was prepared fresh by dissolving 10 µl of a 200 mM stock solution (104.4 mg MUG in 1 ml methanol) in 1 ml of MUG assay buffer. 50 µl of the protoplast extraction supernatant was mixed with 50 µl of the MUG solution in a microtube, and incubated at 37° C. After 0, 1, 2, 3, and 4 hours, 20 µl aliquots were taken and transferred to a tube containing 500 µl of stop buffer (0.2 M $Na_2CO_3$). Samples were read in a Cytofluor II fluorescence multiwell plate reader (Perseptive Biosystems, Framington, Mass.).

Protein determinations were made for the remaining 50 ul of protoplast extraction supernatant using the Standard Protein Assay Kit (BioRad, Richmond, Va.), with bovine albumin dissolved in MUG assay buffer as the standard. Slopes for the GUS enzymatic reaction were determined, and the value of pmoles/minute of GUS activity was corrected to the amount of protein.

Example 27

Southern Blot Analysis of Tobacco

DNA from tobacco plants was extracted according to the methodology of Bernatsky et al., "Toward a Saturated Linkage Map in tomato Based on Isozymes and Random cDNA Sequences," *Genetics* 112: 887–898 (1986), which is hereby incorporated by reference in its entirety.

A fragment of the uidA gene was amplified by PCR, using the primers GUS-F and GUSR1063 described above. Non-radioactive labeling of the probe and hybridization of the membrane were done following the methodology described in detail in Sambrook et al., "Molecular Cloning: A Laboratory Manual (Second Edition)," Cold Spring Harbor, N.Y., Cold Spring Harbor Laboratory Press (1989), which is hereby incorporated by reference in its entirety.

Example 28

Expression of uidA Gene in *Agrobacterium* Cells

*Agrobacterium* cells were initially checked for their potential to express the uidA gene from the different constructs. Cells incubated in SIM medium and then treated with X-Gluc solution, with or without exposure to plant tissue, indicated some level of GUS activity for all the constructs tested except for those containing the PAL promoter from tobacco and the α tubulin from coffee.

Example 29

Expression of uidA Gene in Transformed Tobacco Plants

Figure 10A:
FIGS. 10A–D show activity of GUS in shoots regenerated from tobacco leaves, before being passed into rooting medium.
Figure 10B:
Figure 10C:
Figure 10D:

Transgenic tobacco plants were regenerated containing the T-DNA from the constructs pBI101, pBICa2, pBIαtub, and pBIPAL. Before the rooting step, some shoots were taken for histochemical assays. As shown in FIG. 10A, no activity could be detected in control shoots or shoots transformed with pBIPAL (8x). Shoots resulting from transformation with pBI1011 had GUS activity at the base but very little at the top, as shown in FIG. 10B. Shoots from pBIPAL showed no activity, and shoots from pBICa2 and pBIαtub showed moderate to high GUS activity in all the tissues. FIG. 10C shows strong activity observed in shoot transformed with pBICa2 (8x). FIG. 10D shows moderate activity observed in shoots transformed with pBIαtub (8x).

Figure 11A:
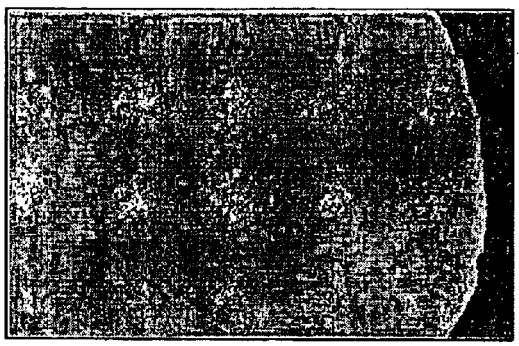
FIGS. 11A–F shows the results of histochemical tests with X-Gluc staining of tobacco leaf discs from the greenhouse.
Figure 11B:
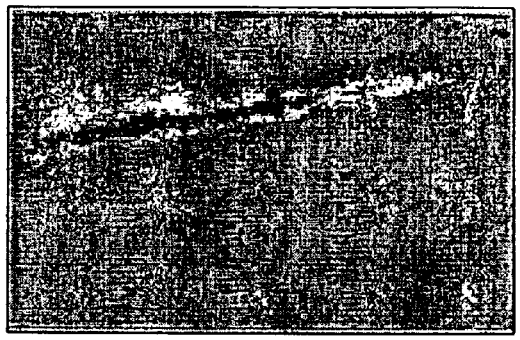
Figure 11C:
Figure 11D:
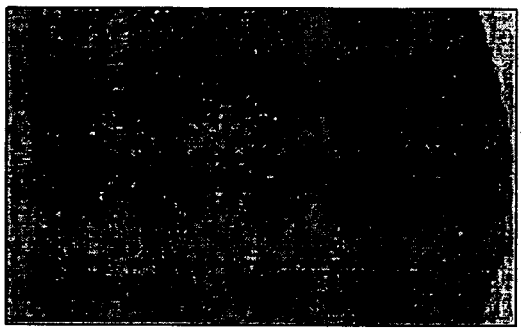
Figure 11E:
Figure 11F:

As shown in FIG. 11A, histochemical assays of transformed greenhouse plants indicated no uidA expression in plants containing pBI101. GUS expression on plants containing pBIαtub was observed to be low, as in FIG. 11B, or moderate, shown in FIG. 11C. Plants containing pBICa2, shown in FIG. 11D, showed high GUS expression. GUS expression in all the leaf tissues was only observed among plants harboring the pBICa2 vector. By observing the intensity of the blue staining in the tissue, it was evident that GUS activity in the plants containing pBIαtub was a fraction of the activity in plants transformed with pBICa2. FIG. 11E shows GUS expression in vascular tissue of plants containing pBIPAL. FIG. 11F shows details of GUS expression on leaf epidermis, vascular tissue and trichomes in plants transformed with pBIαtub.

Example 30

Quantification of GUS Activity

The results with the 4-MUG enzymatic assays indicated a large variability in the GUS activity for the constructs pBICa2 and pBIαtub. Very little, or no activity, was detected for non-transformed plants, and plants containing pBI101 and pBIPAL. Table 9 shows protein activity in transgenic tobacco plants, given as (pmol/minute/mg).

TABLE 9

| Transgenic Line Number | Control | pBI101 | pBICa2 | pBIαtub | pBIPAL |
|---|---|---|---|---|---|
| 1 | 149.12 | 119.72 | 160.39 | 457.70 | 151.91 |
| 2 | 121.33 | 177.64 | 166.34 | 116.28 | 124.73 |
| 3 | 115.38 | 117.59 | 125.54 | 1743.58 | 114.23 |
| 4 | 155.15 | 135.92 | 138.22 | 181.25 | 111.36 |
| 5 | 175.90 | 174.11 | 162.04 | 5650.95 | 194.91 |
| 6 | — | 119.16 | 32290.30 | 132.56 | 155.77 |
| 7 | — | 166.77 | 8335.84 | 784.72 | 156.51 |
| 8 | — | 128.72 | 34676.59 | 195.09 | 146.31 |
| 9 | — | 146.28 | 45403.18 | 158.21 | 112.22 |
| 10 | — | 131.42 | 19420.19 | 4557.97 | 217.91 |
| 11 | — | 152.16 | 41132.02 | 2865.74 | 191.16 |
| 12 | — | 133.90 | 170.12 | 10484.55 | 129.71 |
| 13 | — | 189.01 | 152.07 | 3342.07 | 144.18 |
| 14 | — | 127.05 | 41754.85 | 205.34 | 165.88 |
| 15 | — | 113.35 | 149.69 | 839.56 | 202.74 |
| 16 | — | — | 12138.75 | 166.59 | 175.00 |
| 17 | — | — | 121.91 | 167.75 | 149.15 |
| 18 | — | — | 13212.68 | 136.43 | 149.33 |
| 19 | — | — | 48539.65 | 129.42 | 148.19 |
| 20 | — | — | 7858.51 | 834.79 | 232.08 |
| 21 | — | — | — | — | 169.13 |
| 22 | — | — | — | — | 166.06 |
| 23 | — | — | — | — | 201.27 |
| 24 | — | — | — | — | 117.03 |
| 25 | — | — | — | — | 163.51 |
| 26 | — | — | — | — | 135.28 |
| 27 | — | — | — | — | 143.50 |

GUS activity in the plants containing pBIPAL was expected to be low, because the promoter is inducible. PAL promoters from tobacco have not been characterized to date. From analyses with PAL promoters in other plants, expression of PAL has been found to be very strong in young seedlings just emerging from the seed coat, and decreasing later as the plant grows taller. However, in mature plants, PAL was found active in sepals and pollen grain (Ohl et al., "Functional Properties of a Phenylalanine Ammonia-Lyase Promoter from *Arabidopsis*," *The Plant Cell* 2:837–848 (1990), which is hereby incorporated by reference in its entirety).

Expression of uidA from pBIPAL in previous particle bombardment experiments and protoplast transformations indicates that wounding and cell wall synthesis could act as inducers of the pal B promoter. Observations of GUS activity in vascular tissues of young transgenic plants evidenced low constitutive activity of this promoter in leaves. However, after treating the plant with wounding in combination with crab chitin (1 mg/ml), macerozyme (4%), digested tobacco cell walls, and salicylic acid (1 mM, pH 7.0), no induction of the gene could be observed when X-Gluc histochemical assays were performed. Flowers and roots from selected transformants were also negative after X-Gluc treatment.

Example 31

Effect of uidA Copy Number

Figure 12:
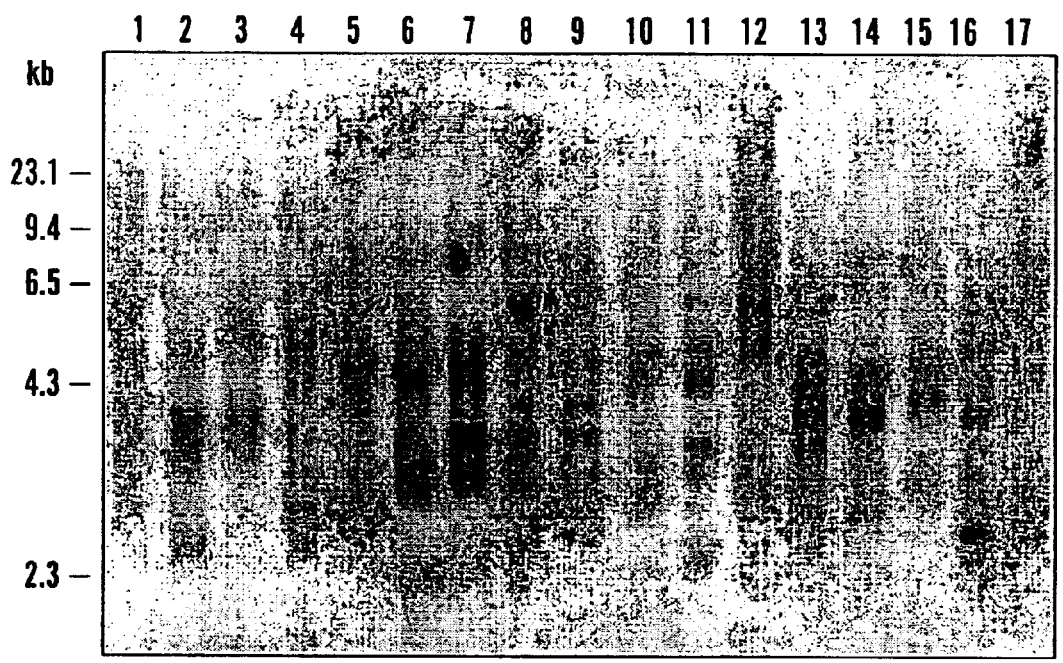
FIG. 12 shows the determination of the uidA copy number in transgenic tobacco plants. A 1273 bp PCR amplified fragment of the uidA gene, labeled with digoxygenin, was used as a probe. 8 µg of HindIII digested genomic DNA were loaded per line. Lambda-Hind III markers are indicated.

The number of uidA insertions into the genome of transgenic plants obtained was determined by Southern blot analysis. These results are shown in FIG. 12. For the different constructs used, uidA copy number varied from 1 to 6 among plants. When the copy number is compared to the GUS activity observed in leaf tissue, there is no indication of any correlation between the two factors. Similar results have been observed in different populations of transgenic plants, where large and apparently random variation in the expression of the transgene occurs (Peach et al., "Transgene Expression Variability (Position Effect) of CAT and GUS Reporter Genes Driven by Linked Divergent T-DNA Promoters," *Plant Molecular Biology* 17:49–60 (1991), which is hereby incorporated by reference in its entirety). The variability is attributed to the effect of the surrounding chromatin on the integration site of the transgene ("position effect"). Also, tandem insertions (Hobbs et al., "Transgene Copy Number can be Positively or Negatively Associated with Transgene Expression," *Plant Molecular Biology* 21:17–26 (1993), which is hereby incorporated by reference in its entirety) and silencing mechanisms (Matzke et al., "Homology-Dependent Gene Silencing in Transgenic Plants: Epistatic Silencing Loci Contain Multiple Copies of Methylated Transgenes," *Molecular & General Genetics* 244:219–229 (1994), which is hereby incorporated by reference in its entirety) may affect the level of expression of a particular transgene. Certainly, position effects and copy number can influence the determination of the actual promoter activity in a plant. From these two variables, only position effect can be eliminated when transient expression is used. Until a site-directed recombination system is developed for plants, extreme variability will continue to be the common factor in transgenic populations and relative promoter strength will be the way to quantify promoter activity.

Since coffee has a long regeneration time, tobacco plants can be used in order to evaluate factors such as strength, tissue specificity, and inducibility of a promoter of interest. However, in the extrapolation of the results of these experiments to coffee, it has to be considered that a heterologous system was used and that there is no information available about the efficacy of integrated doubled CaMV35S promoter (pBICa2) in coffee. Therefore, the final determination of the capacity of a promoter has to be validated in its own homologous system.

The level of α tubulin promoter activity in tobacco is similar to the levels reported in the same plant with the original CaMV35S promoter, and plant promoters such as the bean chalcone synthase promoter (Schmid et al., "Developmental and Environmental Regulation of a Bean Chalcone Synthase Promoter in Transgenic Tobacco," *The Plant Cell* 2:619–631 (1990), which is hereby incorporated by reference in its entirety). As indicated by Kay et al., "Duplication of CaMV35S Promoter Sequences Creates a Strong Enhancer for Plant Genes," *Science* 236:1299–1302 (1987), which is hereby incorporated by reference in its entirety, once a 250 bp sequence was duplicated in the original promoter in order to construct the doubled CaMV35S promoter, a tenfold increase in promoter activity was obtained.

In that sense, although the level of expression obtained by the a tubulin promoter is low in comparison with the doubled CaMV35S promoter, expression in the plant is high in comparison with unmodified promoters. This also suggests that the introduction of changes, through genetic engineering, of the a tubulin promoter can potentially lead to an increase in promoter activity. However, modifications of this sort have not been reported for plant constitutive promoters commonly used, like the rice actin promoter (McElroy et al., "Isolation of an Efficient Actin Promoter for Use in Rice Transformation," *The Plant Cell* 2:163–172 (1990), which is hereby incorporated by reference in its entirety), or the maize ubiquitin promoter (Cornejo et al., "Activity of a Maize Ubiquitin Promoter in Transgenic Rice," *Plant Molecular Biology* 23:567–581 (1993), which is hereby incorporated by reference in its entirety). On the other hand, overexpression of a gene can lead to the silencing phenomenon that was initially observed in petunias, and has been described elsewhere (Matzke et al., "Homology-Dependent Gene Silencing in Transgenic Plants: Epistatic Silencing Loci Contain Multiple Copies of Methylated Transgenes," *Molecular & General Genetics* 244:219–229 (1994), which is hereby incorporated by reference in its entirety). As a consequence, strong promoters used in a transformation system can potentially reduce the frequency of transgenic plants that express adequate amounts of recombinant protein.

The need to increase promoter activity will be finally determined by the nature of the transgene. In the case of developing plants with increased resistance against pathogens and pests, factors, such as translational efficiency (codon preference), mRNA and protein stability, and lethal dose 50% (LD50) can be equally or more important in the final transgenic product than the level of promoter activity itself.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA promoter suitable for inducing expression of a protein encoded by a DNA molecule operably associated with the DNA promoter, wherein said DNA promoter is isolated from coffee and comprises the nucleotide sequence of SEQ ID NO: 1.

2. A DNA construct comprising:

the DNA promoter according to claim 1;

a DNA molecule encoding a protein or polypeptide, wherein the DNA promoter is operably linked 5' to the DNA molecule encoding a protein or polypeptide to induce transcription of the DNA molecule encoding a protein or polypeptide; and a 3' regulatory region operably linked to the DNA molecule encoding a protein or polypeptide.

3. An expression system comprising a vector into which is inserted the DNA construct according to claim 2.

4. A host cell comprising the DNA construct according to claim 2.

5. The host cell according to claim 4, wherein the host cell is a bacterial cell or a plant cell.

6. The host cell according to claim 5, wherein the host cell is an *Agrobacterium* cell.

7. The host cell according to claim 5, wherein the host cell is a plant cell.

8. The host cell according to claim 7, wherein the plant cell is from a plant selected from the group consisting of coffee, alfalfa, rice, wheat, barley, rye, cotton, sunflower, peanut, corn, potato, sweet potato, bean pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

9. The host cell according to claim 8, wherein the plant is coffee.

10. A transgenic plant comprising the DNA construct according to claim 2.

11. The transgenic plant according to claim 10, wherein the plant is selected from the group consisting of coffee, alfalfa, rice, wheat, barley, rye, cotton, sunflower, peanut, corn, potato, sweet potato, bean pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

12. The transgenic plant according to claim 11, wherein the plant is coffee.

13. A transgenic plant seed comprising the DNA construct according to claim 2.

14. The transgenic plant seed according to claim 13, wherein the plant seed is from a plant selected from the group consisting of coffee, alfalfa, rice, wheat, barley, rye, cotton, sunflower, peanut, corn, potato, sweet potato, bean pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

15. The transgenic plant seed according to claim 14, wherein the plant is coffee.

16. A method of making a transgenic plant comprising:
   transforming a plant cell with the DNA construct according to claim 2 and
   regenerating a plant from the transformed plant cell.

17. The method according to claim 16, wherein said transforming is *Agrobacterium* mediated.

18. The method according to claim 16, wherein said transforming comprises:
   propelling particles at the plant cell under conditions effective for the particles to penetrate into the cell interior and
   introducing an expression vector comprising the DNA construct into the plant cell interior.

19. A method of directing protein expression in a plant, said method comprising:
   transforming a plant cell with the DNA construct according to claim 2 to produce a transformed plant cell, and
   regenerating a plant from the transformed plant cell, wherein the DNA molecule encoding a protein or polypeptide is expressed in the plant.

* * * * *